(12) United States Patent
Kim et al.

(10) Patent No.: US 12,364,531 B2
(45) Date of Patent: Jul. 22, 2025

(54) METHODS FOR TREATING SKIN DISORDERS USING PRECISION COOLING TECHNOLOGY

(71) Applicants: RECENSMEDICAL, INC., Ulsan (KR); UNIST(ULSAN NATIONAL INSTITUTE OF SCIENCE AND TECHNOLOGY), Ulsan (KR)

(72) Inventors: Gun-Ho Kim, Ulsan (KR); Weonju Lee, Daegu (KR)

(73) Assignees: RecensMedical, Inc.;, Hwaseong-si (KR); Ulsan National Institute of Science and Technology, Ulsan (KR)

( * ) Notice: Subject to any disclaimer, the term of this patent is extended or adjusted under 35 U.S.C. 154(b) by 699 days.

(21) Appl. No.: 17/590,694

(22) Filed: Feb. 1, 2022

(65) Prior Publication Data
US 2022/0257301 A1    Aug. 18, 2022

(30) Foreign Application Priority Data

Feb. 16, 2021  (KR) .................. 10-2021-0020766
Mar. 9, 2021   (KR) .................. 10-2021-0031073

(51) Int. Cl.
*A61B 18/02*  (2006.01)
*A61B 18/00*  (2006.01)

(52) U.S. Cl.
CPC ............... *A61B 18/0218* (2013.01); *A61B 2018/00029* (2013.01); *A61B 2018/00452* (2013.01); *A61B 2018/00714* (2013.01); *A61B 2018/00791* (2013.01)

(58) Field of Classification Search
CPC ...... A61B 18/0218; A61B 2018/00029; A61B 2018/00452; A61B 2018/00714; A61B 2018/00791
See application file for complete search history.

(56) References Cited

U.S. PATENT DOCUMENTS

| | | |
|---|---|---|
| 2,004,823 A | 6/1935 | Meyer |
| 2,044,823 A | 6/1936 | Whiteside |
| 3,289,749 A | 12/1966 | Crump |
| 4,646,735 A | 3/1987 | Seney |
| 5,976,123 A | 11/1999 | Baumgardner et al. |
| 6,099,521 A | 8/2000 | Shadduck |
| 6,141,985 A | 11/2000 | Cluzeau et al. |
| 6,632,219 B1 | 10/2003 | Baranov et al. |
| 6,669,688 B2 | 12/2003 | Svaasand et al. |
| 7,037,326 B2 | 5/2006 | Lee |

(Continued)

FOREIGN PATENT DOCUMENTS

| | | |
|---|---|---|
| EP | 1030611 B1 | 9/2004 |
| EP | 1401347 B1 | 8/2011 |

(Continued)

OTHER PUBLICATIONS

EP19842037.4 Extended European Search Report dated Apr. 8, 2022.

(Continued)

*Primary Examiner* — Ankit D Tejani
*Assistant Examiner* — Joshua Brendon Solomon
(74) *Attorney, Agent, or Firm* — Knobbe, Martens, Olson & Bear, LLP

(57) ABSTRACT

Disclosed herein are methods of treating skin disorders or relieving dermatological symptoms using precision cooling technology.

26 Claims, 26 Drawing Sheets

(56) References Cited

U.S. PATENT DOCUMENTS

| | | |
|---|---|---|
| 7,780,656 B2 | 8/2010 | Tankovich |
| 7,963,959 B2 | 6/2011 | Da Silva et al. |
| 8,083,734 B2 | 12/2011 | Steinfatt et al. |
| 8,177,827 B2 | 5/2012 | Shapiro |
| 8,256,233 B2 | 9/2012 | Boyden et al. |
| 8,652,131 B2 | 2/2014 | Muller et al. |
| 8,672,879 B2 | 3/2014 | Grant et al. |
| 8,788,060 B2 | 7/2014 | Nebrigic et al. |
| 8,858,583 B2 | 10/2014 | Shtram et al. |
| 9,017,318 B2 | 4/2015 | Fourkas et al. |
| 9,039,688 B2 | 5/2015 | Palmer, III et al. |
| 9,066,712 B2 | 6/2015 | Fourkas et al. |
| 9,113,855 B2 | 8/2015 | Burger et al. |
| 9,398,975 B2 | 7/2016 | Muller et al. |
| 9,522,031 B2 | 12/2016 | Anderson et al. |
| 9,549,773 B2 | 1/2017 | Anderson et al. |
| 9,642,741 B2 | 5/2017 | Feng et al. |
| 9,801,677 B2 | 10/2017 | Anderson et al. |
| 9,855,166 B2 | 1/2018 | Anderson et al. |
| 9,956,355 B2 | 5/2018 | Besirli et al. |
| 9,974,684 B2 | 5/2018 | Anderson et al. |
| 10,085,881 B2 | 10/2018 | Karnik et al. |
| 10,154,870 B2 | 12/2018 | Ottanelli |
| 10,188,444 B2 | 1/2019 | Fourkas et al. |
| 10,213,244 B2 | 2/2019 | Fourkas et al. |
| 10,322,248 B2 | 6/2019 | Besirli et al. |
| 10,363,080 B2 | 7/2019 | Elkins et al. |
| 10,543,032 B2 | 1/2020 | Babkin |
| 11,278,341 B2 | 3/2022 | Kim et al. |
| 2002/0120315 A1 | 8/2002 | Furuno et al. |
| 2004/0102768 A1 | 5/2004 | Cluzeau et al. |
| 2004/0111087 A1 | 6/2004 | Stern et al. |
| 2005/0059940 A1 | 3/2005 | Weber et al. |
| 2006/0200117 A1 | 9/2006 | Hermans |
| 2006/0213509 A1 | 9/2006 | Marin et al. |
| 2007/0005048 A1 | 1/2007 | Niedbala et al. |
| 2007/0239236 A1 | 10/2007 | Manstein |
| 2008/0164296 A1 | 7/2008 | Shelton et al. |
| 2008/0221561 A1 | 9/2008 | Geiger et al. |
| 2009/0036846 A1 | 2/2009 | Dacquay et al. |
| 2009/0062751 A1 | 3/2009 | Newman, Jr. |
| 2009/0163902 A1 | 6/2009 | DeLonzor et al. |
| 2010/0010480 A1 | 1/2010 | Mehta et al. |
| 2010/0087805 A1 | 4/2010 | Citterio et al. |
| 2010/0196343 A1 | 8/2010 | O'Neil et al. |
| 2010/0198207 A1 | 8/2010 | Elkins et al. |
| 2011/0072834 A1 | 3/2011 | Ishikura et al. |
| 2011/0098791 A1 | 4/2011 | Kim |
| 2011/0137268 A1 | 6/2011 | Thomason et al. |
| 2011/0152850 A1 | 6/2011 | Niedbala et al. |
| 2011/0177474 A1 | 7/2011 | Jamnia et al. |
| 2011/0224761 A1 | 9/2011 | Manstein |
| 2012/0130458 A1 | 5/2012 | Ryba et al. |
| 2012/0191166 A1 | 7/2012 | Callister et al. |
| 2012/0232549 A1 | 9/2012 | Willyard et al. |
| 2012/0265278 A1 | 10/2012 | Fourkas et al. |
| 2013/0116719 A1 | 5/2013 | Shtram et al. |
| 2013/0296811 A1 | 11/2013 | Bangera et al. |
| 2013/0315924 A1 | 11/2013 | Hsu et al. |
| 2014/0012226 A1 | 1/2014 | Hochman |
| 2014/0200511 A1 | 7/2014 | Boyden et al. |
| 2014/0277023 A1 | 9/2014 | Sekino et al. |
| 2015/0051545 A1 | 2/2015 | Henderson et al. |
| 2015/0111918 A1* | 4/2015 | Sobotka ............... A61B 18/20 514/183 |
| 2016/0058488 A1 | 3/2016 | Fourkas et al. |
| 2016/0183996 A1 | 6/2016 | Burger et al. |
| 2016/0242956 A1 | 8/2016 | Pilby Gomez |
| 2016/0262820 A1 | 9/2016 | Allison et al. |
| 2016/0279350 A1 | 9/2016 | Besirli et al. |
| 2017/0014174 A1 | 1/2017 | Levine et al. |
| 2017/0062793 A1 | 3/2017 | Zakharyan et al. |
| 2017/0165105 A1* | 6/2017 | Anderson ............... A61F 7/02 |
| 2017/0224935 A1 | 8/2017 | Hoffmann et al. |
| 2017/0231816 A1 | 8/2017 | Ryan |
| 2017/0232243 A1 | 8/2017 | Herweijer |
| 2017/0304558 A1 | 10/2017 | Besirli et al. |
| 2017/0325992 A1* | 11/2017 | DeBenedictis ...... A61K 9/0014 |
| 2017/0348143 A1 | 12/2017 | Rosen et al. |
| 2017/0354451 A1 | 12/2017 | Marin et al. |
| 2018/0116705 A1 | 5/2018 | Lee et al. |
| 2018/0177893 A1* | 6/2018 | Angel ................... A61P 9/00 |
| 2018/0235805 A1 | 8/2018 | Burger et al. |
| 2018/0310979 A1 | 11/2018 | Peled et al. |
| 2019/0000524 A1 | 1/2019 | Rosen et al. |
| 2019/0015146 A1 | 1/2019 | DuBois |
| 2019/0015602 A1 | 1/2019 | Besirli et al. |
| 2019/0038459 A1 | 2/2019 | Karnik et al. |
| 2019/0175394 A1 | 6/2019 | Kim |
| 2019/0175395 A1 | 6/2019 | Kim |
| 2019/0175396 A1 | 6/2019 | Kim |
| 2019/0254866 A1 | 8/2019 | Whiteley et al. |
| 2019/0290881 A1 | 9/2019 | Kim |
| 2020/0054483 A1 | 2/2020 | Kim |
| 2020/0206025 A1 | 7/2020 | Chalberg, Jr. et al. |
| 2021/0113365 A1 | 4/2021 | Kim |
| 2022/0160414 A1 | 5/2022 | Kim et al. |

FOREIGN PATENT DOCUMENTS

| | | |
|---|---|---|
| EP | 2010087 B1 | 11/2014 |
| EP | 2910276 A1 | 8/2015 |
| EP | 2759272 B1 | 11/2018 |
| JP | H0492663 A | 3/1992 |
| JP | H0686818 A | 3/1994 |
| JP | H06321268 A | 11/1994 |
| JP | H10230435 A | 9/1998 |
| JP | 2002505155 A | 2/2002 |
| JP | 2004515270 A | 5/2004 |
| JP | 2005080832 A | 3/2005 |
| JP | 4049358 B2 | 2/2008 |
| JP | 2008212638 A | 9/2008 |
| JP | 2008545462 A | 12/2008 |
| JP | 2009034273 A | 2/2009 |
| JP | 2009056320 A | 3/2009 |
| JP | 2011077314 A | 4/2011 |
| JP | 2012143279 A | 8/2012 |
| JP | 2013142410 A | 7/2013 |
| JP | 2014028130 A | 2/2014 |
| JP | 2014198238 A | 10/2014 |
| JP | 2015510802 A | 4/2015 |
| JP | 2017113635 A | 6/2017 |
| KR | 980005117 U | 3/1998 |
| KR | 19980058500 U | 10/1998 |
| KR | 100200669 B1 | 6/1999 |
| KR | 20030068633 A | 8/2003 |
| KR | 20040093706 A | 11/2004 |
| KR | 20040094508 A | 11/2004 |
| KR | 100786539 B1 | 12/2007 |
| KR | 100790758 B1 | 1/2008 |
| KR | 20080045022 A | 5/2008 |
| KR | 100851274 B1 | 8/2008 |
| KR | 20100041207 A | 4/2010 |
| KR | 20100060222 A | 6/2010 |
| KR | 20100135863 A | 12/2010 |
| KR | 101053835 B1 | 8/2011 |
| KR | 20110119640 A | 11/2011 |
| KR | 20120040760 A | 4/2012 |
| KR | 20120115703 A | 10/2012 |
| KR | 20130087770 A | 8/2013 |
| KR | 101366126 B1 | 2/2014 |
| KR | 101386137 B1 | 4/2014 |
| KR | 20140052667 A | 5/2014 |
| KR | 20140069431 A | 6/2014 |
| KR | 20150030264 A | 3/2015 |
| KR | 20150062492 A | 6/2015 |
| KR | 101577208 B1 | 12/2015 |
| KR | 20160048425 A | 5/2016 |
| KR | 101707659 B1 | 2/2017 |
| KR | 101719459 B1 | 3/2017 |
| KR | 20170041776 A | 4/2017 |
| KR | 20170083399 A | 7/2017 |
| KR | 20170089842 A | 8/2017 |
| KR | 20170130470 A | 11/2017 |

(56) References Cited

FOREIGN PATENT DOCUMENTS

| | | | |
|---|---|---|---|
| KR | 101813652 B1 | 12/2017 | |
| KR | 101819204 B1 | 1/2018 | |
| KR | 101840346 B1 | 5/2018 | |
| KR | 101862127 B1 | 5/2018 | |
| KR | 20180054247 A | 5/2018 | |
| KR | 20180109828 A | 10/2018 | |
| KR | 101936890 B1 | 1/2019 | |
| KR | 20190063724 A | 6/2019 | |
| KR | 20190114710 A | 10/2019 | |
| KR | 20190124971 A | 11/2019 | |
| KR | 20200070095 A | 6/2020 | |
| KR | 20200070139 A | 6/2020 | |
| WO | WO-9220289 A1 | 11/1992 | |
| WO | WO-2016154399 A1 | 9/2016 | |
| WO | WO-2018231868 A1 | 12/2018 | |
| WO | WO-2020022858 A1 | 1/2020 | |

OTHER PUBLICATIONS

KR10-2020-0130588 Office Action dated Apr. 26, 2022 (w/English Translation).
KR10-2020-0130589 Office Action dated Apr. 26, 2022 (w/English Translation).
KR10-2020-0130590 Office Action dated Apr. 26, 2022 (w/English Translation).
Fernandez et al. Cooling effects on nitric oxide production by rabbit ear and femoral arteries during cholinergic stimulation. Br J Pharmacol. 113:550-554 (1994).
Ostadhadi et al. Involvement of nitric oxide in serotonin-induced scratching in mice. Clin Exp Dermatol. 40:647-652 (2015).
PCT/KR2017/012935 International Search Report and Written Opinion dated Jun. 4, 2018.
PCT/KR2017/013901 International Search Report and written opinion dated Aug. 8, 2018.
PCT/KR2018/003773 International Search Report and Written Opinion dated Jul. 6, 2018.
PCT/KR2018/006169 International Search Report and Written Opinion dated Nov. 7, 2018.
PCT/KR2018/016491 International Search Report and Written Opinion dated May 30, 2019.
PCT/KR2019/005105 International Search Report and Written Opinion dated Aug. 14, 2019.
PCT/KR2019009411 International Search Report and Written Opinion dated Nov. 15, 2019.
PCT/KR2019/017328 International Search Report and Written Opinion dated Mar. 27, 2020.
PCT/KR2021/009072 International Search Report and Written Opinion dated Nov. 22, 2021.
Sarifakioglu et al., Evaluating the effects of ice application on the pain felt during botulinum toxin type-a injections: a prospective, randomized, single-blind controlled trial. Ann Plast Surg 53:543-546 (2004).
Smith. Ice anesthesia for injection of dermal fillers. Dermatologic Surgery 36:812-814 (2010).
U.S. Appl. No. 15/828,449 Office Action dated Oct. 2, 2019.
U.S. Appl. No. 16/412,296 Office Action dated Oct. 28, 2020.

\* cited by examiner

Spray Type

Contact Type (a)

(b)

(c)

|  | IFNa | IL-1a | IL-1b | IL-4 | IL-6 | IL-13 | TNFa | TRPA1 | TRPV1 | TRPV4 |
|---|---|---|---|---|---|---|---|---|---|---|
| control | 1 | 1 | 1 | 1 | 1 | 1 | 1 | 1 | 1 | 1 |
| LPA 1uM-24h | 1.4239751 | 1.1458186 | 1.588444 | 1.31904 | 2.281598 | 2.262553 | 2.087518 | 1.123602 | 1.786048 | 3.093954 |
| LPA 3uM-24h | 1.0863261 | 1.2251539 | 1.145058 | 1.010923 | 1.198895 | 1.325014 | 1.909074 | 1.746973 | 1.350176 | 2.732566 |
| LPA 1uM-1weeks | 15.83072 | 2.345359 | 34.28565 | 80.62294 | 14.36189 | 3.174104 | 4.51459 | 2.100482 | 46.89596 | 3.317273 |
| LPA 3uM-1weeks | 33.05273 | 1.408228 | 68.60304 | 186.7008 | 17.00738 | 4.081103 | 2.946795 | 5.97201 | 13.46548 | 2.466031 |

(a)

(b)

(c)

METHODS FOR TREATING SKIN DISORDERS USING PRECISION COOLING TECHNOLOGY

CROSS-REFERENCE

This application claims the benefit of Korean Patent Application No. 10-2021-0020766, filed on Feb. 16, 2021, and Korean Patent Application No. 10-2021-0031073, filed on Mar. 9, 2021.

FIELD OF THE INVENTION

The present specification relates to a skin disease treatment method using precision cooling technology; specifically, it relates to a method for cooling the skin surface while precisely controlling the temperature of the skin surface within a specific temperature range to alleviate symptoms accompanying skin diseases or to treat skin diseases.

BACKGROUND OF THE DISCLOSURE

Skin disease is one of the most common (or typical) diseases in modern society. In particular, some diseases, such as those that are accompanied by constant pain, e.g., atopic dermatitis or itchiness, or those that are notable for their visible symptoms, such as inflammatory acne, are treated as significant diseases that substantially affect daily life, and research for such disease treatment has been actively conducted.

One of the previous methods for skin disease treatment includes cooling the affected area, which is based on the principle that pain can be alleviated in a person via cooling sensation by activating the thermoreceptor of the person. However, in contrast, some studies maintain that with such methods cooling can induce the development of skin diseases. Specifically, studies have revealed that cooling increases the production of nitric oxide in the endothelium, and the produced nitric oxide serves as a medium for serotonin-induced itchiness. (Fernandez N, Monge L, Garcia-Villalon A L, Garcia J L, Gomez B, Dieguez G. Cooling effects on nitric oxide production by rabbit ear and femoral arteries during cholinergic stimulation. Br J Pharmacol. 1994; 113:550–554.) (Ostadhadi S, Haj-Mirzaian A, Azimi E, Mansouri P, Dehpour A R. Involvement of nitric oxide in serotonin-induced scratching in mice. Clin Exp Dermatol. 2015; 40:647-652).

In light of this, while the conceptual idea regarding the level to which cooling may be performed to alleviate the symptoms of skin diseases has been made known, cooling has actually not been performed as a method for treating skin diseases, particularly itchiness or inflammatory acne. This is because it has been possible for the skin tissue to become necrotic due to excessive cooling, posing safety issues, and it has been difficult to find the temperature capable of producing a therapeutic effect. In order to solve these issues, there is a requirement for a precise cooling technology for discovering an appropriate cooling temperature for skin disease treatment and for maintaining an appropriate cooling temperature of the affected area.

SUMMARY OF THE DISCLOSURE

Disclosed herein, in certain embodiments, comprises a method of treating a skin rash or relieving a symptom associated with a skin rash using a cooling device in a subject, comprising: cooling a target skin area affected by the skin rash using the cooling device at a target temperature selected from about −5° C. to about 5° C. for a target cooling time, wherein a temperature of the target skin area is maintained at a temperature with a standard deviation no larger than 3° C. from the target temperature during the target cooling time, wherein the target temperature and the target cooling time are sufficient to reduce an expression of at least one biomarker molecule associated with the skin rash or the symptom.

In some embodiments, the skin rash or the symptom associated with the skin rash comprises atopic dermatitis, itchiness, or acne.

In some embodiments, the target temperature and the target cooling time are sufficient to reduce mRNA or protein expression level of the at least one biomarker by at least 20%, at least 30%, at least 40%, or at least 50%.

In some embodiments, the target skin area is cooled to the target temperature in less than 20 seconds.

In some embodiments, the target cooling time is between about 1 second to about 30 seconds.

In some embodiments, the target cooling time is less than about 5 seconds, less than about 10 seconds, less than about 20 seconds, less than about 30 seconds, or less than about 60 seconds.

In some embodiments, the at least one biomarker molecule is selected from a group consisting of IL-4, IL-10, IL-13, IL-31, TRPV1, TRPA1, IFN-γ, and PAR2.

In some embodiments, the at least one biomarker molecule is selected from a group consisting of IL-1β, IL-6, IL-7, TNFα, MMP1, MMP3, and MMP9.

In some embodiments, the at least one biomarker molecule comprises IL-31, and the target temperature and the target cooling time are sufficient to reduce mRNA or protein expression level of IL-31 by at least 30%.

In some embodiments, the skin target area has less than about 2 cm in diameter, or has a size of less than about 7 cm2.

In some embodiments, the symptom associated with the skin rash is relieved for at least a day after the treatment to the subject, determined by a visual analogue scale (VAS) score of the subject.

In some embodiments, the cooling device comprises a temperature sensor, a cryogen, and a control module, the method further comprising: detecting the temperature of the target skin area by the temperature sensor; and maintaining the temperature of the target skin area by a control module configured to control a temperature of the cooling medium based on the temperature of the target skin area during the operation of the cooling device.

In some embodiments, the cooling device further comprises a guide unit and a nozzle, wherein the method further comprises detecting a distance from the target skin area to the nozzle using the guide unit.

In some embodiments, the cryogen comprises CO2, liquid nitrogen, NO2, NO, N2O, HFC, methane, PFC, or SF6.

In some embodiments, the cooling the target skin area comprises spraying the cooling medium directly to the target skin area through the nozzle.

In certain embodiments, there is provided a method of reducing an expression of at least one biomarker molecule related to itching using a cooling device capable of cooling with a target temperature for a preset time duration, the method comprising: preparing the cooling device comprising a housing, a temperature sensor, a control module, and a nozzle, wherein the control module is configured to control a temperature of a cryogen which is transferred from a container to the nozzle according to a detected temperature by the temperature sensor; positioning the cooling device on a patient's skin such that a skin target area is defined; cooling the skin target area such that a temperature of the skin target area reaches the target temperature, which comprises spraying the cryogen to the skin target area directly; and maintaining the temperature of the skin target area at the target temperature for the preset time duration, which comprises detecting the temperature of the skin target area, and increasing or decreasing the temperature of the cryogen when the temperature of the skin target area is lower or higher than the target temperature while the cryogen is consistently sprayed; wherein the target temperature is selected from −5° C. to 5° C. such that the expression of at least one biomarker molecule selected from a group consisting of interleukin-4, interleukin-10, interleukin-13, and interleukin-31 at the skin target area is reduced.

In some embodiments, during the preset time duration, the temperature of the skin target area is maintained at a temperature with a standard deviation no larger than 3° C. from the target temperature.

In some embodiments, the cooling time is selected below 20 seconds.

In some embodiments, the method further comprises: setting the target temperature and the preset time duration by using an input module of the cooling device.

In some embodiments, the target temperature is set as 0° C. and the preset time duration is set as 5 seconds when the skin target area is a part of patient's face.

In some embodiments, the target temperature is set as −5° C. and the preset time duration is set as 5 seconds when the skin target area is a part of patient's body.

In some embodiments, the method further comprises: removing the cooling device from the skin target area or moving to another skin target area when a notification is provided such that the skin target area is cooled for the preset time duration only, wherein the notification is provided when the preset time duration is past after the temperature of the skin target area reaches the target temperature.

In some embodiments, the method further comprises: reducing expression of at least one biomarker molecule selected from a group consisting of interleukin-4 mRNA, interleukin-10 mRNA, interleukin-13 mRNA, and interleukin-31 mRNA.

In some embodiments, the method further comprises: reducing an expression of at least one biomarker molecule selected from a group consisting of interleukin-4 protein, interleukin-10 protein, interleukin-13 protein, and interleukin-31 protein.

In some embodiments, the method further comprises: reducing an expression of at least one biomarker molecule selected from a group consisting of TRPV1, TRPA1, IFN-γ, and PAR2.

DETAILED DESCRIPTION OF THE DISCLOSURE

Figure 1:
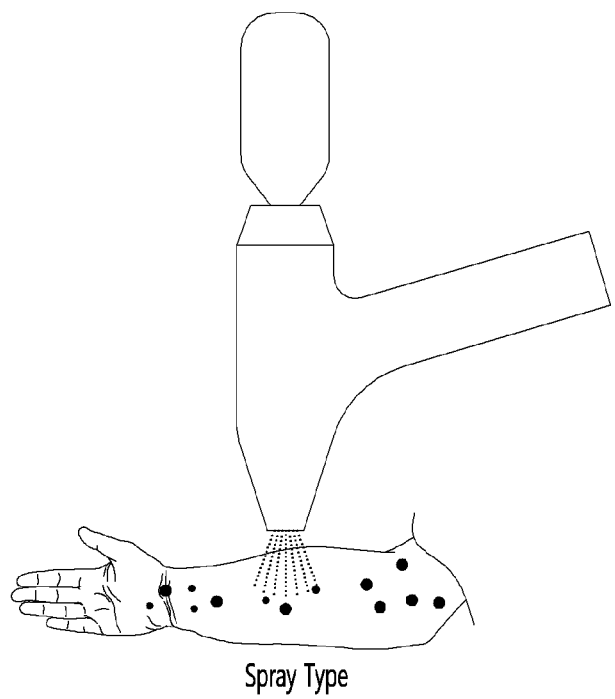
FIG. 1 is a view showing a skin disease treatment method using a precision cooling technology according to an embodiment of the present specification.
Figure 1:
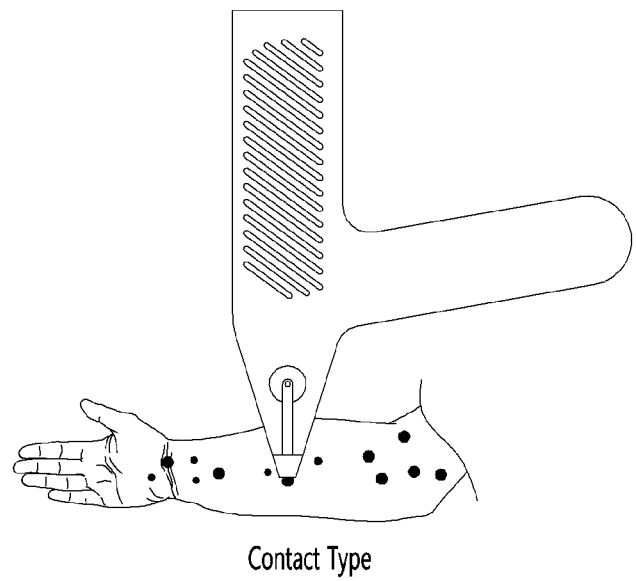

The above-mentioned objects, features and advantages of the present specification will become more apparent from the following detailed description in conjunction with the accompanying drawings. However, since the present specification may undergo various changes and may have various embodiments, specific embodiments will be exemplified in the drawings and described in detail below.

As a general rule, the same reference numbers will be used to describe the same elements throughout the specification. In addition, components or steps shown in the drawings of each embodiment that have the same function within the scope of the same idea will be described using the same reference numbers, and overlapping descriptions thereof will be omitted.

Numbers (for example, first, second, etc.) used in the description of the present specification are only identifiers for distinguishing one component from other components.

Unless specifically stated or clear from the context, the term "about" in reference to a numerical value may be understood to mean the stated numerical value and up to +/−10% of the numerical value; the term "about" in the context of a numerical range may be understood to mean a range from a value 10% below the lower limit of the numerical range to a value 10% higher than the upper limit of the numerical range.

In the following embodiments, the singular expression comprises the plural expression unless the context clearly dictates otherwise.

In the following embodiments, terms such as 'include' or 'have' mean that the features or components described in the specification exist; this does not preclude the possibility that one or more other features or components may be added.

In cases where certain embodiments may be implemented otherwise, a specific process may be performed in a different order than described. For example, two processes described in succession may be performed substantially simultaneously, or may be performed in an order opposite to the order described.

The present specification relates to a treatment method using precision cooling technology. More specifically, it relates to a method for treating a skin disease or alleviating symptoms accompanying a skin disease by maintaining an affected area with a skin disease within a specific temperature range for a specific time to reduce or suppress the expression of a biomarker involved in the skin disease in the affected area.

The skin diseases described in the present specification refer to various diseases occurring on the skin of the human body and hair, sweat glands, etc. related to the skin. Specifically, the skin diseases include systemic skin diseases such as atopic dermatitis, seborrheic dermatitis, allergic contact dermatitis, eczema, and itching, and local skin diseases such as acne, moles, and corns. Furthermore, "skin disease" may be understood to constitute a concept encompassing a skin rash in which the color, shape, or texture of the skin changes. Hereinafter, a method of treating specific skin diseases such as itchiness, atopic dermatitis, and inflammatory acne using precision cooling technology will be described; however, the technical spirit of the present specification is not limited thereto, and may be equally applied to other skin diseases.

The precision cooling technology described in this specification refers to a technology for precisely controlling the temperature of a target area in cooling a target area such as an affected area or skin. Specifically, precision cooling technology may refer to a technique of cooling the temperature of the target area to a target temperature and maintaining the temperature of the target area at the target temperature for a cooling time. To this end, the precision cooling technology may include a feedback system that periodically measures the temperature of the target area and reflects the measured temperature data to control the temperature of the target area.

The target area may refer to an area in which the cooling treatment method is performed. For example, the target area may refer to an area in which a coolant is sprayed in a cooling treatment method using a spray-type cooling device to be described later. For another example, the target area may refer to an area in contact with a cooling medium in a cooling treatment method using a contact-type cooling device to be described later. The size of the target area may be selected according to the design of the cooling device for performing the cooling treatment method. For example, the size of the target area may be selected within a diameter of 10 mm to 100 mm or an area of 50 mm$^2$ to 100 cm$^2$. As a result, the target area may be specified as an area comprising a skin disease on the skin surface. For example, the target area may be specified as an area on the skin surface where a symptom of itchiness is felt, an area comprising atopic dermatitis, an area comprising inflammatory acne, and the like.

The target temperature may be selected from various temperature ranges. For example, the target temperature may be selected from about −20° C. to about 30° C. Alternatively, the target temperature may be selected from about −15° C. to about 30° C. Alternatively, the target temperature may be selected from about −10° C. to about 30° C. Alternatively, the target temperature may be selected from about −5° C. to about 30° C. Alternatively, the target temperature may be selected from −5° C. to about 20° C. Alternatively, the target temperature may be selected from −5° C. to about 10° C., about −10° C. to about 5° C., or about −5° C. to about 5° C.

The cooling time may be selected from various time ranges. For example, the cooling time may be selected from a time range of greater than or equal to about 1 second and less than or equal to about 300 seconds. Alternatively, the cooling time may be selected from a time range of about 5 seconds or more and about 300 seconds or less. Alternatively, the cooling time may be selected from a time range of about 10 seconds or more and about 300 seconds or less. Alternatively, the cooling time may be selected from a time range of about 20 seconds or more and about 300 seconds or less.

The cooling time may be selected based on the target temperature. For example, when the target temperature is selected to be about −10° C. or less, the cooling time may be selected to be about 20 seconds or less. Alternatively, when the target temperature is selected from about −10° C. to about −5° C., the cooling time may be selected from about 30 seconds or less. Alternatively, when the target temperature is selected from about −5° C. to about 0° C., the cooling time may be selected from about 60 seconds or less. Alternatively, when the target temperature is selected from about 0° C. or higher, the cooling time may be selected from about 300 seconds or less. If the cooling time is selected based on the target temperature, it is possible to prevent the recipient from feeling pain due to cooling in the cooling treatment.

The target temperature and cooling time may be selected based on the treatment site. For example, when the target area is specified as a part of the face, the target temperature may be selected to be about 0° C., and the cooling time may be selected to be about 5 seconds. As another example, when the target area is specified as a part of the body having a thicker skin layer than the face, the target temperature may be selected to be about −5° C., and the cooling time may be selected to be about 5 seconds. In other words, different target temperatures and/or different cooling times may be selected to produce the same effect for two target areas with different degrees of transfer of cooling energy.

Meanwhile, maintaining the temperature of the target area at the target temperature during the cooling time may refer to controlling the temperature of the target area within a preset threshold value from the target temperature during the cooling time.

In this case, the threshold value may be selected within a range of 1° C. to 10° C. For example, it can refer to a process in which, if the target temperature is 0° C., the cooling time is 5 seconds, and the threshold value is 5° C., the treatment method using the precision cooling technique is to maintain the temperature of the target area at −5° C. or higher and 5° C. or lower for 5 seconds.

Alternatively, the threshold value is selected within a range of 1° C. to 10° C., and may be understood as a standard deviation value. For example, if the target temperature is −5° C., the cooling time is 10 seconds, and the threshold value is 5° C., the treatment method using the precision cooling technology may refer to the process of maintaining the temperature of the target area so that the standard deviation is 5° C. based on the target temperature of −5° C. for 10 seconds.

Alternatively, the threshold value may be understood as a temperature change rate with time. Specifically, the threshold value may be selected within a range of 1° C./sec to 30° C./sec. For example, if the target temperature is 5° C., the cooling time is 20 seconds, and the threshold value is 5° C./sec, the treatment method using the precision cooling technology may refer to a process in which the instantaneous change in the temperature of the target area is within 5° C./sec.

Meanwhile, the above-described precision cooling technology may be implemented using a cooling device. Cooling devices can be broadly divided into two types, and these will be described in detail below.

FIG. 1 is a diagram showing a method of treating a skin disease using a precision cooling technology according to an embodiment of the present specification. Referring to FIG. 1, the precision cooling technology may be divided into a method using a spray-type cooling device and a method using a contact-type cooling device.

The spray-type cooling device may refer to a device for spraying a coolant. For example, the operator may perform cooling of the affected area by spraying a coolant onto the affected area of the person to be treated using a spray-type cooling device. The operation of the spray-type cooling device will be described in detail later. As the coolant sprayed from the cooling device, a material capable of applying cooling energy to the target area may be used, such as carbon dioxide, liquid nitrogen, nitrogen dioxide (NO2), nitrogen monoxide (NO), nitrogen dioxide (N2O), HFC-based substances, methane, PFC, SF6, cooling water, cooling gas, etc.

Here, it may be preferable to select carbon dioxide as a coolant for cooling treatment for skin diseases. For example, when the coolant sprayed on the skin surface is carbon dioxide for alleviating itching, the acidity of the skin may be optimized by the carbon dioxide penetrating into the skin to form carbonated water. Through this, additional effects other than cooling such as suppressing the proliferation of unnecessary microorganisms can be derived; in relieving itching, using carbon dioxide as a coolant over other substances can be an advantage.

In addition, carbon dioxide may make it easier to maintain the target area at the above-described target temperature compared to other materials. For example, liquid nitrogen has a relatively lower temperature (for example, about −196° C. at 1 atm) than solid carbon dioxide (for example, about −78.5° C. at 1 atm) at the same atmospheric pressure. Accordingly, when liquid nitrogen is used to maintain the temperature of the target area in a temperature range of −20° C. to 30° C., which is the maximum range in which the above-described target temperature can be selected, it is necessary to control the temperature of the sprayed coolant using more thermal energy than solid carbon dioxide.

Furthermore, since carbon dioxide has a colorless and odorless property, there is no awkwardness or discomfort that the recipient may feel in spraying it, and as a result, it is possible to provide a stable treatment to the recipient as compared to other substances.

Hereinafter, the structure of the spray-type cooling device for spraying the above-described coolant will be described.

According to an embodiment of the present specification, the spray-type cooling device may include a coolant container, a conduit, a valve, a nozzle, a temperature control unit, a control module, a temperature sensor, an input/output module, and a guide unit. The spray-type cooling device may further comprise a housing in which the above-described components are disposed.

The coolant container may store coolant. For example, the coolant may be compressed at a high pressure and stored in a coolant container. The coolant container is fluidly connected with the conduit such that coolant in the coolant container can move through the conduit to the nozzle. The coolant container may be disposable. For example, the coolant container may be temporarily attached to a cooling device to provide coolant, and as the coolant in the container is depleted, it may be removed from the cooling device and disposed of.

The conduit may provide a flow path for the coolant to travel. For example, a conduit may be disposed between the coolant container and the valve and between the valve and the nozzle so that coolant can travel through the conduit from the coolant to the valve and from the valve to the nozzle.

A valve may control the spray of coolant. For example, the valve may receive a signal from a control unit to open or close, and coolant may or may not be sprayed accordingly.

The nozzle may control the flow amount, flow rate, or pressure of the coolant. For example, the nozzle may include a structure in which the inner diameter becomes smaller in one direction, and the coolant may be adiabatically expanded while passing through the nozzle to be sprayed at a low temperature.

The temperature control unit may control the temperature of the coolant. For example, the temperature control unit may include a heating unit, and may provide thermal energy to the coolant through the heating unit. For example, the temperature control unit may include a thermo-electric module that converts electrical energy into thermal energy, and may receive electric power to provide heat to the outside. The temperature control unit may receive a signal from the control module and decrease the thermal energy provided to the coolant to decrease the temperature of the coolant or increase the provided heat energy to increase the temperature of the coolant. The temperature control unit may be disposed inside or outside the conduit between the nozzle and the valve to apply thermal energy to the coolant moving from the valve to the nozzle. Alternatively, the temperature control unit may be disposed inside or outside the conduit between the valve and the coolant container to apply thermal energy to the coolant moving from the coolant container to the valve.

The control module may control the valve and the temperature control unit. The control module may open or close the valve by receiving an input signal from the input/output module. The control module may control the temperature control unit by receiving information on the target temperature and cooling time from the input/output module.

The input/output module may receive an input from the operator and output a notification to the operator. Specifically, the input/output module may include an input module for receiving various types of inputs, comprising button input, key input, touch input, and voice input, and an output module for outputting various types of information in a visual and/or audible form. Here, the input module is a comprehensive concept that comprises a button that the operator can press, a touch sensor that detects the operator's touch, a microphone that receives the operator's voice input, and various types of input means that detect or receive various types of inputs. In addition, the output module is a comprehensive concept comprising a display that outputs an image, a speaker that outputs a sound, a haptic device that generates vibration, and other various types of output means.

The temperature sensor may measure a temperature at a predetermined distance. For example, the temperature sensor is an infrared sensor, and a distance and a temperature measurement range for measuring temperature may be determined based on an optical lens included in the infrared sensor. As another example, the temperature sensor is a thermal imaging camera, and a temperature measurement distance and a temperature measurement range may be determined based on an optical lens included in the camera. The cooling device may measure the temperature of the target area using a temperature sensor.

The guide unit may define a coolant spray distance of the cooling device. Precise temperature control of the target area according to an embodiment of the present specification requires accurate temperature measurement of the target area; to this end, the coolant needs to be sprayed while the positional relationship between the cooling device and the target area is fixed. The guide unit may maintain a state in which the cooling device is spaced apart from the target area by a preset spray distance. For example, as will be described later, the operator may operate the cooling device while the guide unit of the cooling device is in contact with the target area. In this case, the spray distance may be understood as the distance from the nozzle end of the cooling device to the guide unit end, and from the nozzle end of the cooling device to which the coolant is sprayed to the target area.

Meanwhile, the degree of inclination of the central axis of the temperature sensor with respect to the central axis of the nozzle may be determined based on the length of the guide unit. For example, the angle between the central axis of the temperature sensor and the central axis of the nozzle may be specified so that a point where the central axis of the nozzle and the central axis of the temperature sensor meet corresponds to the end of the guide unit. Accordingly, the target area may be located at a point spaced apart from the temperature sensor by the measurement distance.

The spray-type cooling device is not limited to comprising only the above-described configuration, and may further include a configuration necessary to perform the cooling treatment method in addition to this.

Hereinafter, a cooling treatment method using a spray-type cooling device to which the above-described precision cooling technology is applied will be described.

Figure 2:
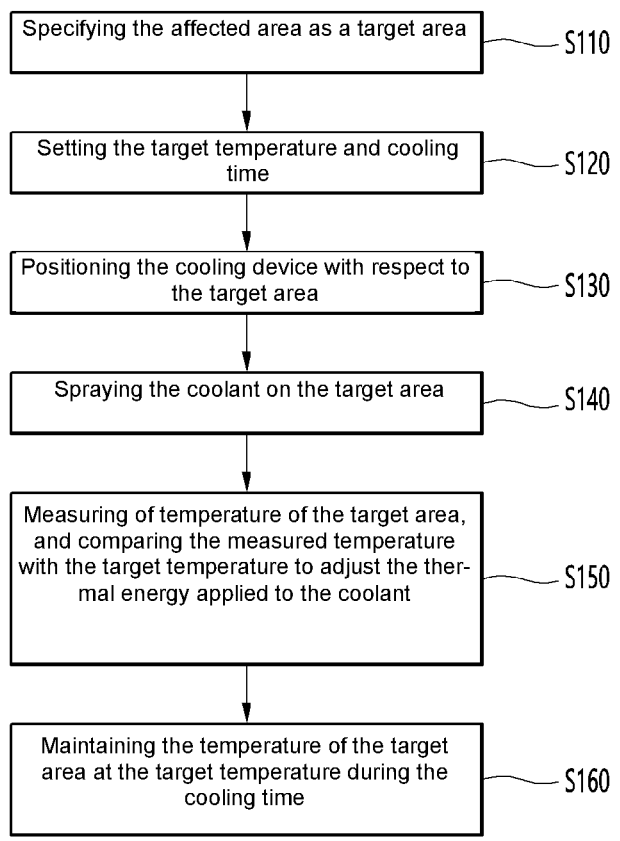
FIG. 2 is a view showing a flow chart related to a method for cooling the affected area using a spray-type cooling device according to an embodiment of the present specification.

FIG. 2 is a view showing a flow chart related to a method for cooling the affected area using the spray-type cooling device according to an embodiment of the present specification.

Referring to FIG. 2, the cooling treatment method may comprise the following processes: specifying the affected area as a target area (S110), setting the target temperature and cooling time (S120), positioning the cooling device with respect to the target area (S130), spraying the coolant on the target area (S140), measuring the temperature of the target area, comparing the measured temperature with the target temperature to adjust the thermal energy applied to the coolant (S150), and maintaining the temperature of the target area at the target temperature during the cooling time (S160). Hereinafter, each step will be described in detail.

The operator may specify the affected area to be subjected to cooling treatment as a target area (S110). The operator can visually determine, through a separate examination, or at the request of the recipient, select the affected area to be subjected to cooling treatment and specify it as the target area. Alternatively, an image of the recipient's skin is obtained using a separate device such as a camera or a thermal imaging camera, the acquired image may be analyzed to detect an affected area, and the detected area may be specified as a target area. Here, the target area may refer to the surface of the skin suspected of having a disease.

The operator may set the target temperature and cooling time (S120). The operator may set a specific cooling temperature and a specific cooling time depending on the type of skin disease of the affected area, and input these to the cooling device. The cooling device may receive and store the input of the target temperature and cooling time from the operator, and may operate based on the stored target temperature and cooling time later. Also, this process may be omitted. For example, the operator may arbitrarily set the target temperature and cooling time in the cooling device itself without separately setting the target temperature and cooling time, or may use a preset target temperature and cooling time.

The operator may position the cooling device with respect to the target area (S130). The operator may position the cooling device in the target area by bringing the guide unit of the cooling device into contact with the target area. The operator may position the cooling device in the target area such that the nozzle direction or the coolant spray direction of the cooling device is perpendicular to the target area. In this case, more accurate temperature measurement and temperature control of the target area may be possible in the cooling device.

The operator may operate the cooling device to spray the coolant onto the target area (S140). When the input/output module of the cooling device receives an input from the operator, the control module may control the valve to spray the coolant. In this case, the cooling device may control the temperature of the coolant sprayed based on a preset initial temperature.

The cooling device may measure the temperature of the target area, compare the measured temperature with the target temperature, and adjust the thermal energy applied to the coolant (S150). The control module of the cooling device may compare the measured temperature with the set target temperature with respect to the target temperature obtained from the temperature sensor. When the measured temperature is lower than the target temperature, the control module of the cooling device increases the thermal energy applied to the coolant by using the temperature control unit; if the measured temperature is higher than the target temperature, the thermal energy applied to the coolant may be reduced by using the temperature control unit. In this case, the PID control method may be used in increasing/decreasing thermal energy applied to the coolant.

According to the above-described temperature control method of the cooling device, the temperature of the target area may be the target temperature. When the temperature of the target area reaches the target temperature, the cooling device may provide a notification to the operator through the input/output module. In this case, the cooling device may provide a start notification when the temperature measured for the target area is within a preset error value based on the target temperature. The preset error value may be selected from 0.1° C. to 5° C. For example, when the set target temperature is 0° C. and the error value is 0.5° C., the cooling device may determine that the temperature of the target area has reached the target temperature when the measured target area temperature is −0.5° C. or more and 0.5° C. or less.

The cooling device may maintain the temperature of the target area as the target temperature during the cooling time (S160). The cooling device may maintain the temperature of the target area as the target temperature for a set cooling time by periodically repeating the process of measuring the temperature of the target area and controlling the thermal energy applied to the coolant. On the other hand, the meaning of the phrasing that the temperature of the target area is being maintained at the target temperature during the cooling time may indicate that the temperature of the target area is adjusted to within a preset threshold value from the target temperature during the cooling time. For example, when the temperature of the target area reaches the target temperature, the cooling device operates a timer set to the cooling time; if the temperature of the target area deviates from the target temperature below or above the threshold value before the timer expires, the timer is terminated or reset, and if the temperature of the target area does not deviate from the target temperature below or above the threshold value before the timer expires, a completion notification may be provided when the timer expires.

The operator may change the target area or end the cooling treatment after maintaining the temperature of the target area at the target temperature for a cooling time according to the above-described process. For example, when the operator receives the completion notification described above, the cooling device may move from the existing target area to the specified affected area as the next target area. In another example, when the cooling time elapses after the temperature of the target area reaches the target temperature, by stopping the coolant spray or increasing the temperature of the coolant spraying, it is possible to prevent overcooling of the target area or causing pain due to cooling.

Referring back to FIG. 1, the contact-type cooling device may use a contact cooling method in which a cooling medium is brought into contact with a target area to cool it.

According to an embodiment of the present specification, the contact-type cooling device may comprise a cooling medium, a temperature control unit, a control module, a temperature sensor, and an input/output module. The contact-type cooling device may further comprise a housing in which the above-described components are disposed. Hereinafter, the configurations of the contact-type cooling device will be described, but descriptions of parts overlapping with the configuration of the above-described spray-type cooling device, for example, the control module and the input/output module, will be omitted.

The cooling medium may be thermally coupled to the target area. For example, the cooling medium may transfer cooling energy by directly contacting the target area or indirectly contacting the target area through a separate heat transfer member such as a tip.

The temperature control unit may control the temperature of the cooling medium. For example, the temperature control unit may comprise a heat absorbing unit, absorb heat from the cooling medium through the heat absorbing unit, and consequently provide cooling energy to the cooling medium. Here, the meaning of providing cooling energy to the object may be understood as a meaning of lowering the temperature of the object by cooling the object. Specifically, the temperature control unit may comprise a thermoelectric module that converts electrical energy into thermal energy, and may receive electric power to provide cooling energy to the outside. The temperature control unit may receive a signal from the control module and increase the cooling energy provided to the cooling medium to decrease the temperature of the cooling medium or decrease the provided cooling energy to increase the temperature of the cooling medium. The temperature control unit may be thermally coupled with the cooling medium to provide cooling energy to the cooling medium.

The temperature sensor may measure the temperature of the cooling medium. For example, the temperature sensor is a contact-type temperature sensor, thermally coupled to the cooling medium to measure the temperature of the cooling medium, and provide the measured temperature information to the control module.

The contact-type cooling device is not limited to include only the above-described configuration, and may further comprise a configuration necessary for performing the cooling treatment method in addition to this.

Figure 3:
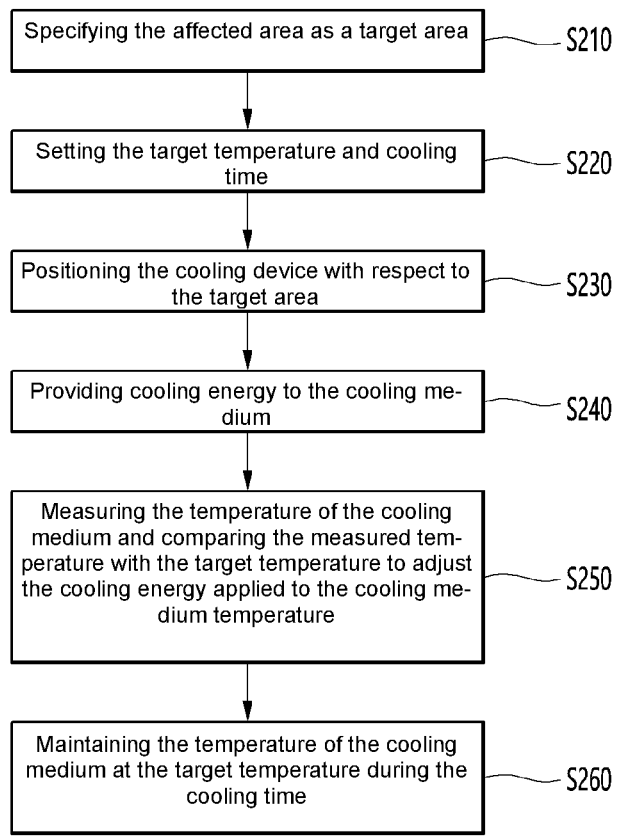
FIG. 3 is a diagram showing a flow chart related to a method for cooling the affected area using a contact-type cooling device according to an embodiment of the present specification.

FIG. 3 is a view showing a flow chart related to a method for cooling the affected area using a contact-type cooling device according to an embodiment of the present specification.

Referring to FIG. 3, the cooling treatment method may comprise the following processes: specifying the affected area as a target area (S210), setting the target temperature and cooling time (S220), positioning the cooling device with respect to the target area (S230), providing cooling energy to the cooling medium (S240), measuring the temperature of the cooling medium and comparing the measured temperature with the target temperature to adjust the cooling energy applied to the cooling medium (S250), and maintaining the temperature of the cooling medium at the target temperature during the cooling time (S260). Hereinafter, each step will be described in detail, but the parts overlapping with those described in the cooling treatment method using the spray-type cooling device will be omitted.

The operator may specify the affected area to be subjected to cooling treatment as a target area (S210). This step overlaps with the part described in the cooling treatment method using the spray-type cooling device and is omitted.

The operator may set the target temperature and cooling time (S220). This step overlaps with the part described in the cooling treatment method using the spray-type cooling device and is omitted. However, in the case of using the contact-type cooling device, the temperature of the cooling medium thermally connected to the target area is measured without directly measuring the temperature of the target area, so that, in consideration of the difference between the temperature of the target area and the temperature of the cooling medium, the target temperature may be set lower than the temperature range in which the effect is proven in an experiment to be described later. For example, in the case of using the contact-type cooling device, the target temperature may be set lower than that in the case of using the spray-type cooling device, by about 1° C. to about 10° C. in consideration of the thermal resistance due to the contact.

The operator may position the cooling device with respect to the target area (S230). The operator may bring the cooling medium or the cooling tip of the cooling device in contact with the target area. The operator may bring the cooling device into contact with the target area so that the central axis of the cooling tip is perpendicular to the target area. In this case, more accurate temperature measurement and temperature control of the target area may be possible in the cooling device.

The operator may operate the cooling device to provide cooling energy to the cooling medium (S240). When the input/output module of the cooling device receives an input from the operator, the control module may transmit cooling energy to the cooling medium using the temperature control unit.

The cooling device may measure the temperature of the cooling medium and adjust the cooling energy applied to the cooling medium by comparing the measured temperature and the target temperature (S250). The control module of the cooling device may compare the temperature of the cooling medium obtained from the temperature sensor with the set target temperature. When the measured temperature of the cooling medium is lower than the target temperature, the control module of the cooling device reduces the cooling energy applied to the cooling medium by using the temperature control unit; when the measured temperature of the cooling medium is higher than the target temperature, the cooling energy applied to the cooling medium may be increased by using the temperature control unit. In this case, the PID control method may be used in increasing/decreasing cooling energy applied to the cooling medium.

According to the above-described temperature control method of the cooling device, the temperature of the cooling medium may be the target temperature. The cooling device may provide a notification to the operator through the input/output module when the temperature of the cooling medium reaches the target temperature. In this case, the cooling device may provide a start notification when the measured temperature of the cooling medium is within a preset error value based on the target temperature. The preset error value may be selected from 0.1° C. to 5° C. For example, if the set target temperature is 0° C. and the error value is 0.5° C., the cooling device may determine that the temperature of the cooling medium has reached the target temperature when the measured temperature of the cooling medium is −0.5° C. or more and 0.5° C. or less.

The cooling device may maintain the temperature of the cooling medium at the target temperature during the cooling time (S260). The cooling device may measure the temperature of the cooling medium and periodically repeat the process of controlling the cooling energy applied to the cooling medium to maintain the temperature of the cooling medium at the target temperature for a set cooling time. In this case, the meaning of the phrasing that the temperature of the target area is being maintained at the target temperature during the cooling time may indicate that the temperature of the target area falls within a preset threshold value from the target temperature during the cooling time. For example, when the temperature of the cooling medium reaches the target temperature, the cooling device operates the timer set for the cooling time, and if the temperature of the cooling medium deviates from the target temperature below or above the threshold before the timer expires, the timer is terminated or reset, while if the temperature of the cooling medium does not deviate from the target temperature below or above the threshold before the timer expires, a completion notification may be provided when the timer expires.

The operator may change the target area or end the cooling treatment after maintaining the temperature of the cooling medium at the target temperature for the cooling time according to the above-described process. For example, when the operator receives the completion notification described above, the cooling device may move from the existing target area to the specified affected area as the next target area. As another example, when the cooling time elapses after the temperature of the cooling medium reaches the target temperature, the cooling device stops supplying cooling energy to the cooling medium or increases the temperature of the cooling medium, so that it is possible to prevent pain caused by overcooling or cooling of the target area.

Above, the case of using a spray-type cooling device and a contact-type cooling device in a cooling treatment method using a precision cooling technology has been described. The contact-type cooling device monitors the temperature of the target area indirectly, for example, by replacing the temperature of the cooling medium with the temperature of the target area, because it is difficult to measure the temperature of the target area as described above. By contrast, the spray-type cooling device measures the temperature of the target area directly so it may be more suitable for precise temperature control of the target area.

Hereinafter, for convenience of explanation, a case in which cooling treatment is performed using a spray-type cooling device using carbon dioxide will be described; however, the technical spirit of the present specification is not limited thereto, and may be similarly applied even when a contact-type cooling device is used.

1. Itching

Hereinafter, an experiment to prove the effect of relieving itching through the cooling treatment method using the above-described precision cooling technology will be described in detail. Through the experimental results to be described later, it has been proven that when treating itching with the cooling treatment method using the precision cooling technology according to an embodiment of the present specification, the itching is greatly relieved and the itching relief effect lasts for a prescribed period of time.

(1) VAS Score Evaluation

1) Experimental Example a. Selection of Test Subjects

Among the patient group with symptoms of atopic dermatitis, patients with mild to severe symptoms of atopic dermatitis, specifically, patients with Eczema Area Severity Index scores of less than 13, were selected as experimental subjects. At this time, pregnant, lactating, or patients sensitive to cooling were excluded from the experiment.

In addition, patients treated with systemic steroids or antihistamines within the past 4 weeks or with topical steroids or antibiotics within the past 2 weeks were excluded from the study.

In addition, the use of other drugs within the study period was prohibited. A total of 28 patients (22 males, 6 females) were selected as study subjects and the study was completed; the average age of the subjects was 29.0±9.0 years.

b. Experimental Method

A clinical study was conducted for two months on the experimental subjects. For Group 1 among the experimental subjects, cooling treatment was performed using a cooling device (Recensmedical, Cryo-VIVE, Korea); for Group 2 among the experimental subjects, excluding Group 1, observation was performed as a control group without cooling treatment.

For the experimental subjects in Group 1, treatment was carried out by spraying a coolant on the affected area for atopic dermatitis for about 5 seconds using a cooling device so that the affected area for atopic dermatitis (a circular affected area with a diameter of about 15 mm) was maintained at −5° C.

The above-mentioned cooling treatment was performed once a week for a total of 8 weeks.

The cooling treatment method performed in the experiment comprises a step of specifying the area suspected of itching as the target area, setting the target temperature to −5° C. and setting the cooling time to 5 seconds; a step of disposing a cooling device relative to the target area; a step of operating the cooling device to spray a coolant on a target area, and applying thermal energy to the coolant using a temperature control means of the cooling device; a step of maintaining the temperature of the target area at −5° C. by measuring the temperature of the target area, so that if the measured temperature is lower than −5° C., the heat energy applied to the coolant per unit time is increased, and if the measured temperature is higher than −5° C., the thermal energy applied to the coolant per unit time is reduced; and a step of terminating the cooling treatment for the target area when the time the temperature of the target area is maintained at −5° C. is at least 5 seconds. In this case, in the step of maintaining the target area at the target temperature of −5° C., the temperature of the target area is maintained within the threshold range from −5° C. (for example, the threshold range is selected from 1° C. to 10° C.). Also, the diameter of the affected area specific to the target area is about 15 mm.

2) Method of Analysis

Visual analogue scale (VAS) scores for itching were evaluated at 10 minutes, 30 minutes, and 60 minutes, respectively, after cooling treatment was performed on the experimental subjects in Group 1. VAS is one of the widely used measurements to measure properties that have a range over a series of values and that cannot be easily measured. In this experiment, the VAS score was evaluated for the degree of itching.

In addition, using the same method, the VAS score (visual analogue scale) for itching was continuously evaluated at 1 week, 2 weeks, and 8 weeks after the start of cooling treatment. The VAS score (visual analogue scale) for itching at 1 week, 2 weeks, and 8 weeks after the initiation of cooling treatment was evaluated using data from 12 subjects who completed the study scheduled for 2 months.

For the experimental subjects in Group 2, the VAS score was evaluated at the same time point as the evaluation time of the VAS score for the experimental subjects in Group 1.

In addition, satisfaction with the cooling treatment was evaluated for the experimental subjects in Group 1. Specifically, the satisfaction of the experimental subjects was evaluated using a 5-grade questionnaire consisting of worse, poor, moderate, good, and excellent.

Statistical analysis of VAS scores was performed using the Statistical Package for the Social Sciences (SPSS) version 18.0 (SPSS, Inc., Chicago, IL, USA).

In addition, the difference in VAS scores according to time in each experimental group was evaluated using repeated measured ANOVA.

Hereinafter, the experimental results derived according to the above-described analysis method with reference to FIGS. 4 to 7 will be described in detail.

3) Analysis Result

A. VAS Score Result

Figure 4:
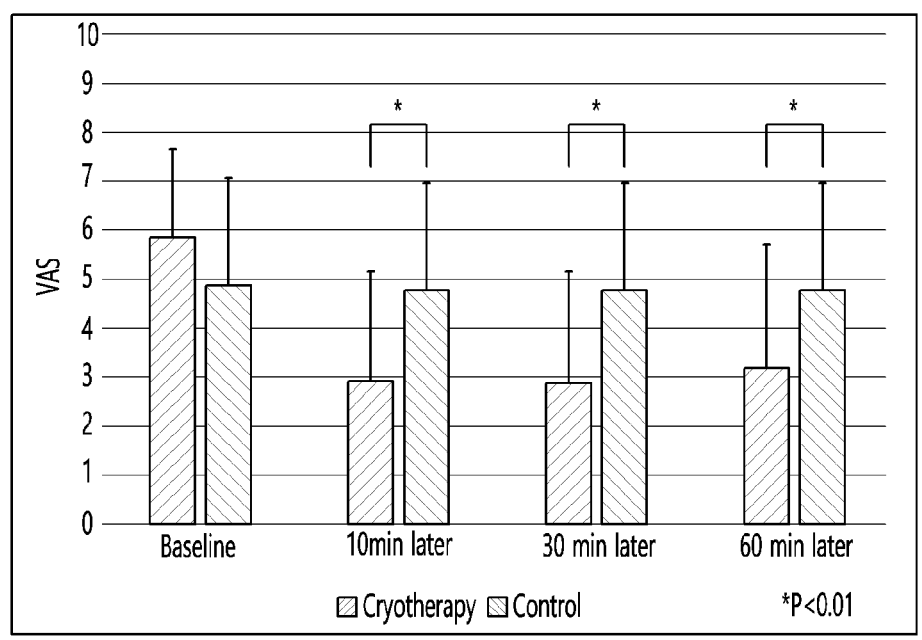
FIGS. 4 to 6 are graphs showing the effect of the cooling treatment method for itchiness or atopy according to an embodiment of the present specification.

Referring to FIG. 4, it can be seen that the VAS score for itching of Group 1 (hereinafter, the treatment group) on the day of the cooling treatment was relatively lower than that of Group 2 (hereinafter, the control group).

Specifically, before cooling treatment was performed, the treatment group had a VAS score of 5.86±1.80 and the control group had a VAS score of 4.86±2.19. Before cooling treatment, it can be seen that the treatment group had a relatively high VAS score. That is, it can be confirmed that the itching was more severe in the treatment group than in the control group before cooling treatment was performed.

After 10 minutes of cooling treatment, the treatment group had a VAS score of 2.89±2.25 and the control group had a VAS score of 4.79±2.17.

After 30 minutes of cooling treatment, the treatment group had a VAS score of 2.86±2.31 and the control group had a VAS score of 4.79±2.17.

After 30 minutes of cooling treatment, the treatment group had a VAS score of 3.18±2.53 and the control group had a VAS score of 4.79±2.17.

At this time, the data of the VAS score was calculated in the form of mean±standard deviation (SD).

At each time point after cooling treatment, the VAS score of the treatment group was evaluated as a relatively lower value than the VAS score of the control group. That is, it can be confirmed that the itching was more severe in the treatment group than in the control group before cooling treatment, but after cooling treatment, the itching was not more severe in the treatment group than in the control group. That is, it can be confirmed that the itching in the treatment group improved more within the same period.

Figure 5:
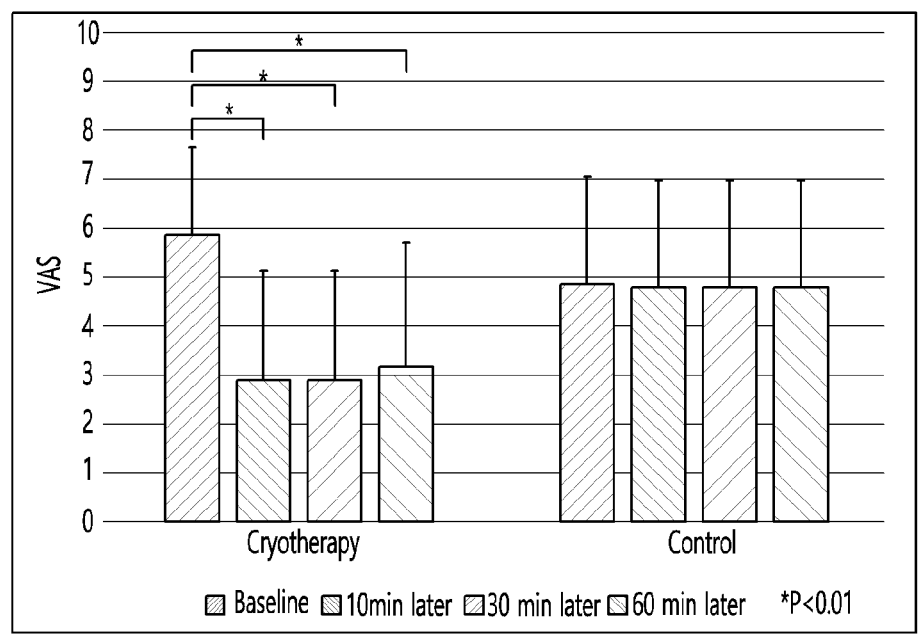

Referring to FIG. 5, it can be seen that the VAS score of the treatment group at all time points decreased to a relatively large value before cooling treatment, that is, compared with the baseline. On the other hand, it can be seen that the VAS score of the control group at all time points decreased to a relatively small value before cooling treatment, that is, compared with the baseline.

According to the analysis results of FIGS. 4 and 5, it can be seen that the cooling treatment according to an embodiment of the present specification provides a short-term itching relief effect. Specifically, it can be seen that a relatively low VAS score is maintained compared to the baseline for at least 60 minutes after cooling treatment, and thus the itching relief effect is maintained.

Figure 6:
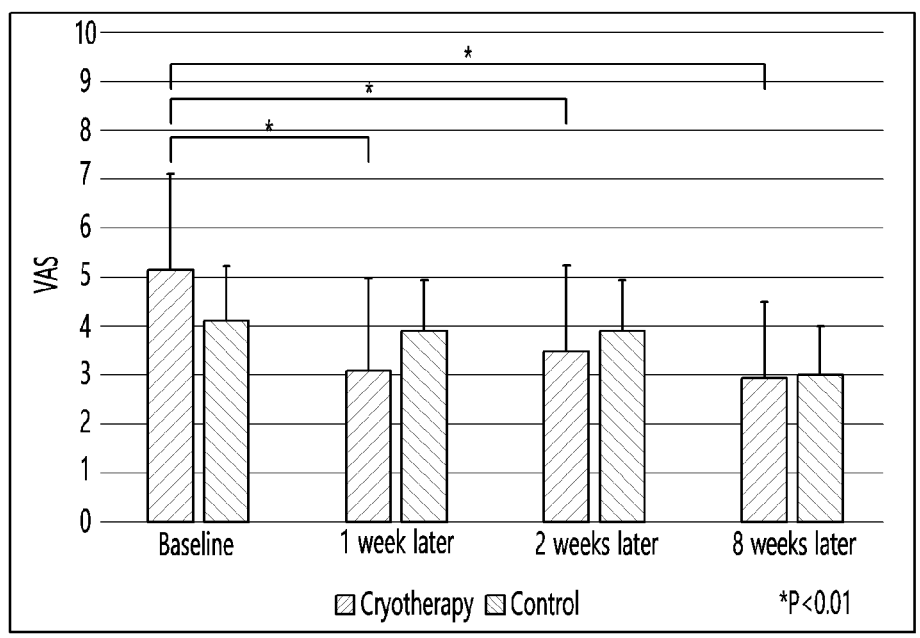

Referring to FIG. 6, it can be seen that the VAS score of the treatment group is reduced compared to before cooling treatment, even after a certain period of time has elapsed after cooling treatment.

Specifically, before cooling treatment, the VAS score of the treatment group was evaluated to be 5.86±1.80; the VAS score of the treatment group after 1 week of cooling treatment was 3.18±1.88, the VAS score of the treatment group after 2 weeks was 3.50±1.78, and the VAS score of the treatment group after 8 weeks was 2.92±1.51.

That is, it can be seen that at all time points, a statistically significant decrease in the VAS score was observed compared to the baseline before the cooling treatment was performed.

According to the analysis result of FIG. 6, when cooling treatment is performed using the itching treatment method according to an embodiment of the present specification, it can be seen that it has been proven that the itching relief effect is maintained even after a certain period of time as well as immediately after cooling treatment.

4) Discussion

Considering the experimental results, cooling treatment that maintains the affected area at −5° C. for at least 5 seconds effectively relieves the itchiness of the affected area in that the VAS score is lowered, and maintains the relief effect for a certain period of time in that the low VAS score is maintained immediately after the cooling treatment and until 8 weeks thereafter.

On the other hand, in the prior art, when cooling treatment for an itching-affected area was performed, the itching relief effect was not great, and even if there was a relief effect, the effect was limited immediately after the cooling treatment was performed. Moreover, in the prior art, studies have indicated that the itching symptoms do not improve but increase when cooling treatment is performed on the itching affected area. It is expected that the prior art performs cooling without precise temperature control, so that the effect is insignificant.

Therefore, the cooling treatment method of maintaining the affected area at −5° C. for 5 seconds using the precise temperature control technology according to an embodiment of the present specification has critical significance in that it has an itching relief effect and its ability to last is excellent compared to the prior art.

Hereinafter, an animal experiment to prove the effect of relieving itching through the cooling treatment method using the above-described precision cooling technology will be described in detail. As will be described later, the cooling treatment method using precision cooling technology is able to reduce the expression of biomarkers related to itching in the target area for performing cooling, Accordingly, it can be proven that the cooling treatment method using precision cooling technology relieves itching and maintains the relief effect.

Additionally, based on the results of animal experiments to be described later, in reducing the expression of biomarkers in the target area through the cooling treatment method using the precision cooling technology, the critical significance of the target temperature for cooling the target area and the critical significance of the cooling time for maintaining the temperature of the target area at the target temperature will also be described.

(2) Animal Experimentation

As confirmed through the analysis results of animal experiments to be described later, the target temperature and/or cooling time in performing cooling treatment for symptoms of itchiness are factors that greatly affect the itchiness alleviation effect.

Therefore, in order to generate a therapeutic effect for itching, the target temperature for cooling the target area and/or the cooling time for maintaining the temperature of the target area at the target temperature must be very finely controlled. The present specification is meaningful in that an optimal target temperature and/or cooling time was found to relieve itching.

Hereinafter, in relation to the method for treating itching according to an embodiment of the present specification, the target temperature and/or cooling time at which the therapeutic effect is significantly increased will be described in detail.

1) Experimental Example

Hereinafter, in accordance with an embodiment of the present specification with reference to FIGS. 7 to 15, an experimental example for demonstrating the effect of a treatment method for alleviating itchiness by cooling a target area will be described in detail. Through the experimental results to be described later, it was confirmed that the itching alleviation effect is increased when cooling treatment is performed on the target area at a specific target temperature and a specific cooling time according to the itching treatment method according to an embodiment of the present specification.

In this experimental example, to treat lysophosphatidic acid (LPA)-induced itching in mice, a cooling device capable of controlling temperature and time was used to cool the itching-related area. Cooling treatment was performed using a cooling device (Recensmedical, Cryo-VIVE, Korea) capable of temperature and time control. Meanwhile, cooling treatment was performed through a cooling method in which a carbon dioxide coolant was sprayed on the itch-related area.

In addition, in this experimental example, using real-time polymerase chain reaction (PCR) and immunohistochemistry, the expression level of biomarkers before and after cooling treatment was investigated.

Protease activated receptor 2 (PAR2; 1:100 dilution; Invitrogen),

Transient receptor potential vanilloid 1 (TRPV1; 1:1000 dilution; Abcam),

Transient receptor potential A1 (TRPA1; 1:100 dilution; Abcam),

Transient receptor potential M8 (TRPM8 1:100 dilution; Abcam),

Cathepsin S (1:100 dilution; Abcam)

Interferon gamma (IFN-γ 1:200 dilution; Novusbio)

IL-4 (1; 400 dilution; Invitrogen),

IL-10 (1; 200 dilution; abeam),

IL-13 (1; 200 dilution; abeam),

IL-31 (1; 200 dilution; abeam)

The above-described biomarkers can be considered as biomarkers related to itching and atopic dermatitis. In particular, interleukins 4, 10, 13, and 31, which are cytokines, constituting signaling substances, can be considered as direct factors causing a person to feel itching caused by skin diseases. Specifically, in itching or atopic dermatitis, when the human body receives a specific external stimulus, the above-described immune response occurs in which interleukin is secreted, the person feels itching by the secreted interleukin, and the person self-stimulates the affected area; as a result, interleukin is secreted again, resulting in a vicious cycle. At this time, if the production or expression of interleukin 4, 10, 13, and 31, which causes itching, is suppressed, it is at least possible to prevent a person from applying stimulation to the affected area by themselves, thereby preventing the vicious cycle structure described above.

In addition, the TRP (Transient receptor potential) channel is an ion channel expressed in various tissues such as neurons, skin, heart, respiratory tract, kidney, etc., and is known as a medium for transmitting itching; a significant increase in its expression has been confirmed in patients complaining of itching. Therefore, when the expression of TRP channels, particularly TRPV1, and TRPA1 is suppressed or reduced, it can be seen that the itching felt by the patient is also alleviated. On the other hand, TRPM8 is a TRP channel that can feel a low temperature, and a method of activating the TRPM8 channel with menthol or the like has been introduced to relieve itching. In the experimental results to be described later, the expression of the TRPM8 channel, like other biomarkers, is reduced or suppressed; as a result, it can be seen that suppression of expression of other biomarkers contributes to itching relief regardless of activation of the TRPM8 channel.

On the other hand, while the cooling temperature to be described later may be applied identically to an actual human, it may be slightly changed because the thickness and body heat of the skin of mice and the human skin are different.

Figure 7:
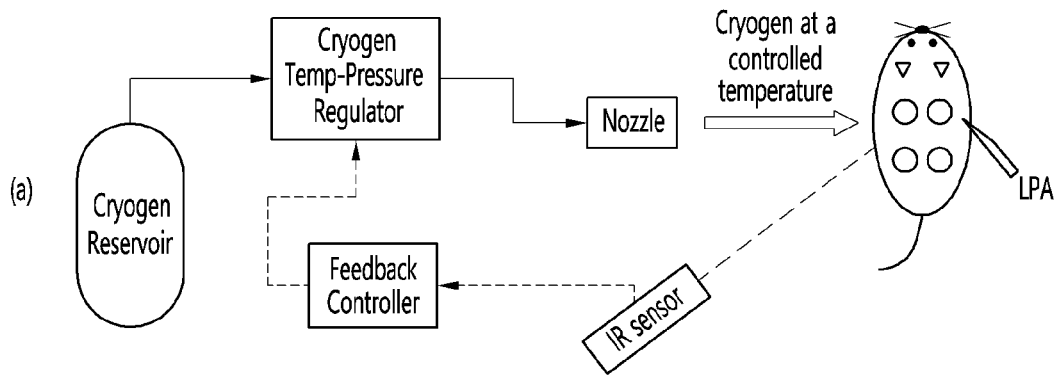
FIGS. 7 and 8 are diagrams showing an animal experiment design for confirming the degree of suppression of expression of related biomarkers according to cooling treatment for itchiness or atopy according to an embodiment of the present specification.
Figure 7:
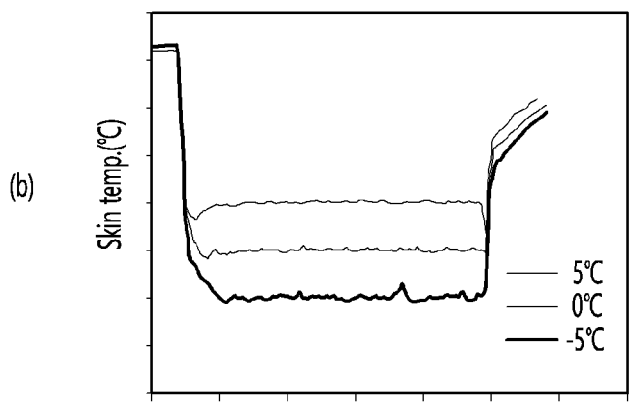
Figure 7:
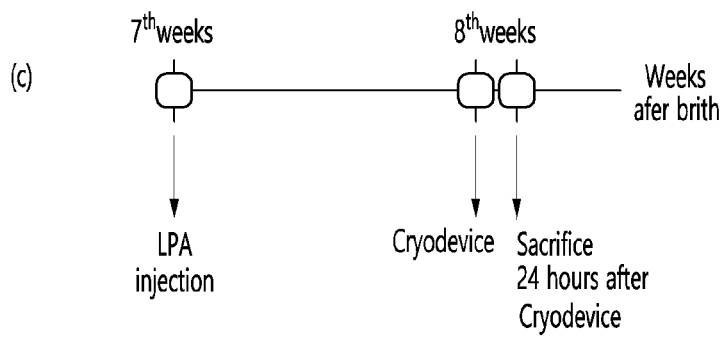

FIG. 7 is a diagram showing a schematic diagram of an experimental schema of an itchiness induction model according to an embodiment of the present specification.

Six-week-old female HR-1 mice (HR-1; SLC Inc., Hamamatsu, Japan) were acclimatized to cages for 1 week. Then, 10 μl of lysophosphatidic acid (LPA) at a concentration of 3 μM, known to induce atopic dermatitis, was injected intradermally into 2 sites on the back of 7-week-old female HR-1 mice using a 30-gauge syringe). A cooling treatment was performed using a cooling device at the time point one week after LPA injection. Specifically, cooling treatment was performed for 5 seconds, 10 seconds, or 20 seconds at −5° C., 0° C., or 5° C. temperature conditions for two affected areas located on the back of LPA-injected mice. At this time, cooling treatment was performed on two mice under the same conditions for each cooling condition.

For the cooling treatment, a cooling device (Recensmedical, Cryo-VIVE, Korea) capable of temperature and time control was used. Specifically, a cryogenic substance (e.g., carbon dioxide) was sprayed onto the area to be injected of the LPA injection solution, that is, the affected area suspected of itching, but the thermodynamic state (e.g., temperature and/or pressure) of the cryogenic substance was controlled by applying heat to the cryogenic substance. In addition, by measuring the temperature of the affected area in real time with an IR sensor, and performing feedback control based on the difference between the preset cooling target temperature and the real-time measured temperature, the heat applied to the cryogenic material was adjusted so that the temperature of the affected area was maintained at a preset target temperature. As a result, the cooling treatment was performed while precisely controlling the temperature of the affected area within the target temperature to be cooled.

On the other hand, in order to compare the effect of cooling treatment, a group that did not perform cooling treatment on LPA-injected mice and a group that did not receive LPA injection were prepared as controls.

For an optimal experiment, an experiment was additionally performed to determine the LPA concentration and LPA treatment time.

Specifically, each mouse was scarified at the following time points: ① When 24 hours had elapsed since injecting 10 ul of LPA of 1 uM concentration into 2 mice; ② When 1 week had elapsed since injecting 10 ul of LPA of 1 uM concentration into 2 mice; ③ When 24 hours had elapsed since injecting 10 ul of LPA of 3 uM concentration into 2 mice; and ④ When 1 week had elapsed since injecting 10 ul of LPA of 3 uM concentration into 2 mice; then the RNA was isolated, and the expression of itching and atopy-related genes was compared.

Figure 8:
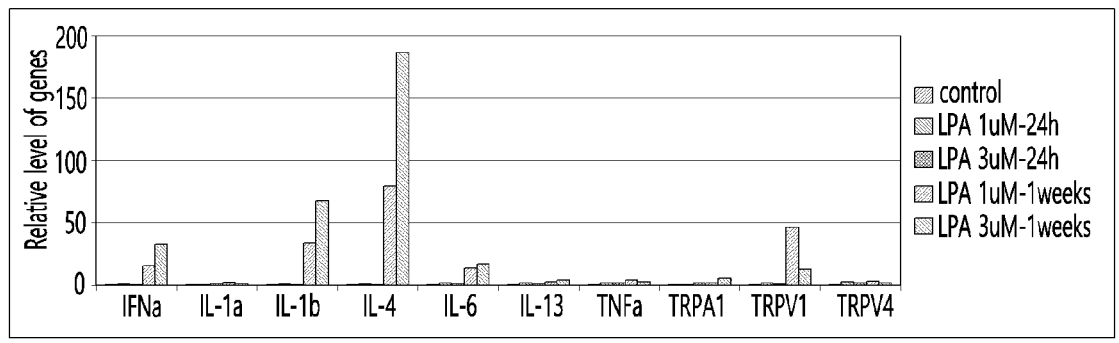

FIG. 8 is a graph and table showing the results of experiments for determining LPA concentration and LPA treatment time.

Referring to FIG. 8, it was observed that, at a point in time one week after injection of 3 uM LPA 10 ul, the expression of most genes related to itching and atopy, such as IFN-gamma, IL-1a, IL-1b, IL-4, IL-6, IL-13, TRPA1, and TRPV1, was relatively significantly increased.

Therefore, at a time point one week after the injection of 3 uM LPA 10 ul, each mouse was scarified, RNA was isolated, and analyses of itching gene expression, itching protein expression analysis, and immunohistostaining analysis, which will be described later, were performed.

2) Method of Analysis

A. Real-Time PCR Analysis

At one week after the cooling treatment was performed, each mouse was scarified and RNA was isolated.

From the isolated RNA, total RNA was isolated using TRIzol reagent. In addition, cDNA was synthesized from 3 mg of total RNA using a cDNA synthesis kit (Promega, Madison, WI, USA) comprising ImProm-II™ reverse transcriptase and oligo-dT primers.

50 ng of synthesized cDNA; 10 pM specific oligonucleotide primers for TRPA1, TRPV1, TRPM8, PAR2, IL-4, IL-10, IL-13, IL-31 and IFN-γ; and Power SYBR Green premix (Applied Biosystems, Foster City, CA, USA) were used to perform real-time PCR in duplicate.

The PCR primers used for PCR analysis are as follows.

| Gene | Direction | Sequence |
|---|---|---|
| mouse GAPDH | Forward | AACTTTGGCATTGTGGAAGG |
| | Reverse | ACACATTGGGGGTAGGAACA |
| mouse TRPA1 | Forward | CCATGACCTGGCAGAATACC |
| | Reverse | TGGAGAGCGTCCTTCAGAAT |
| mouse TRPV1 | Forward | TTCAGTGCTGGAGGTGATCG |
| | Reverse | ATCTGTCCCACTTGTCCTGC |
| mouse TRPM8 | Forward | TGCTGGAGTGGAACCAGTTG |
| | Reverse | AGAGCCGTGAACATGACCTC |
| mouse PAR2 | Forward | GTGGCTGCTGGGAGGTATC |
| | Reverse | AGTGATTGGAGGCTGGGTTTC |
| mouse IL-4 | Forward | TGACCGACATCGAAGACATGC |
| | Reverse | AGCATAGGGTGGGTCAAATAGG |
| mouse IL-10 | Forward | GGATTGCACTTTCGAAGACATG |
| | Reverse | GGATTGCACTTTCGAAGACATG |
| mouse IL-13 | Forward | GGGACATGGTTTGCTGCCTA |
| | Reverse | AGACAGGAGTGTTGCTCTGG |
| mouse IL-31 | Forward | TGCAGCTTGTCCTTCGGTG |
| | Reverse | TGCTGATGGCCTGATTGTCTT |

Cycling conditions for amplification were performed as follows.

Amplification was performed for 10 min at 95° C., 40 cycles for 15 s at 95° C., and 60 s at 60° C.

PCR products were evaluated with the Step one Plus (Applied Biosystems), a real-time PCR analysis software.

B. Immunohistochemical Analysis

Tissue samples associated with affected area of itching were obtained from each mouse and placed in a cryomold with embedding medium. Tissue samples were frozen at −80° C., cut to a thickness of 7 μm and fixed with 4% paraformaldehyde and 0.1% Triton X-100 for 10 minutes. After 1 hour treatment with 5% normal donkey serum (Jackson ImmunoResearch), incubation was performed overnight with antibodies against TRPA1 (1:100 dilution; Abcam), TRPV1 (1:1000 dilution; Abcam), TRPM8 (1:100 dilution; Abcam), PAR2 (1:100 dilution; Invitrogen), IL-4 (1; 400 dilution; Invitrogen), IL-10 (1; 200 dilution; Abcam), IL-13 (1; 200 dilution; Abcam), IL-31 (1; 200 dilution; Abcam) and IFN-γ (1:200 dilution; Novusbio).

Thereafter, the tissue sample was washed three times with phosphate-buffered saline, and incubated with donkey anti-rabbit horseradish peroxidase-conjugated antibody (1:100; Amersham, Buckinghamshire, UK) for 1 hour.

At this time, 3-amino9-ethylcarbazole (DAKO, Glostrup, Denmark) was used as a color developing reagent for horseradish peroxidase (HRP). In addition, the slides were counterstained with hematoxylin for 10 minutes and then counterstained with DAPI for 10 minutes. The above-described procedures were performed in duplicate.

Statistical analysis of each analysis result was performed using SPSS version 18.0 (SPSS, Inc., Chicago, IL, USA).

In addition, repeated ANOVA was performed for each analysis result.

3) Analysis Result

Figure 9:
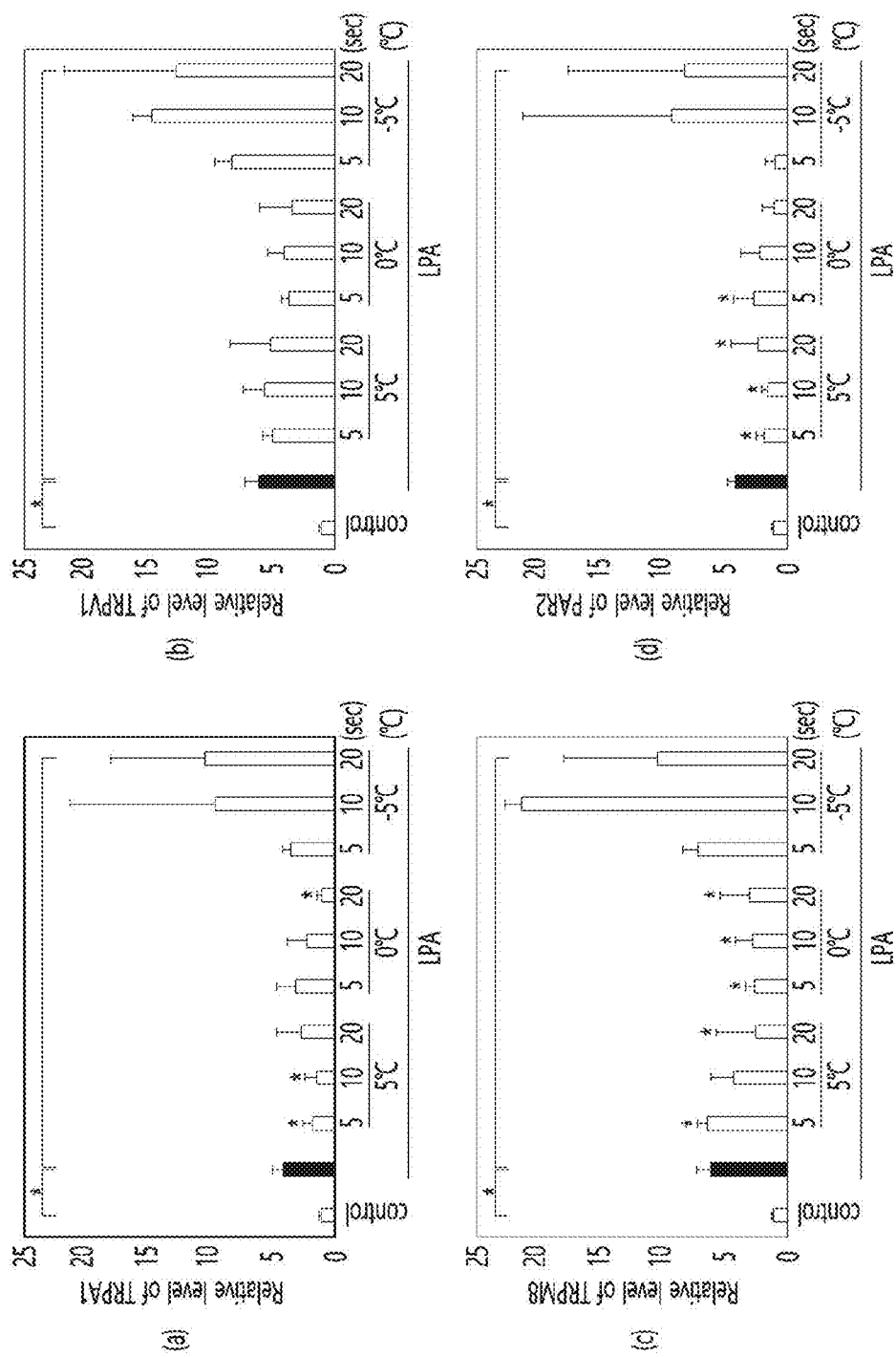
FIGS. 9 to 15 are diagrams showing the results of animal experiments related to itchiness or atopy.
Figure 10:
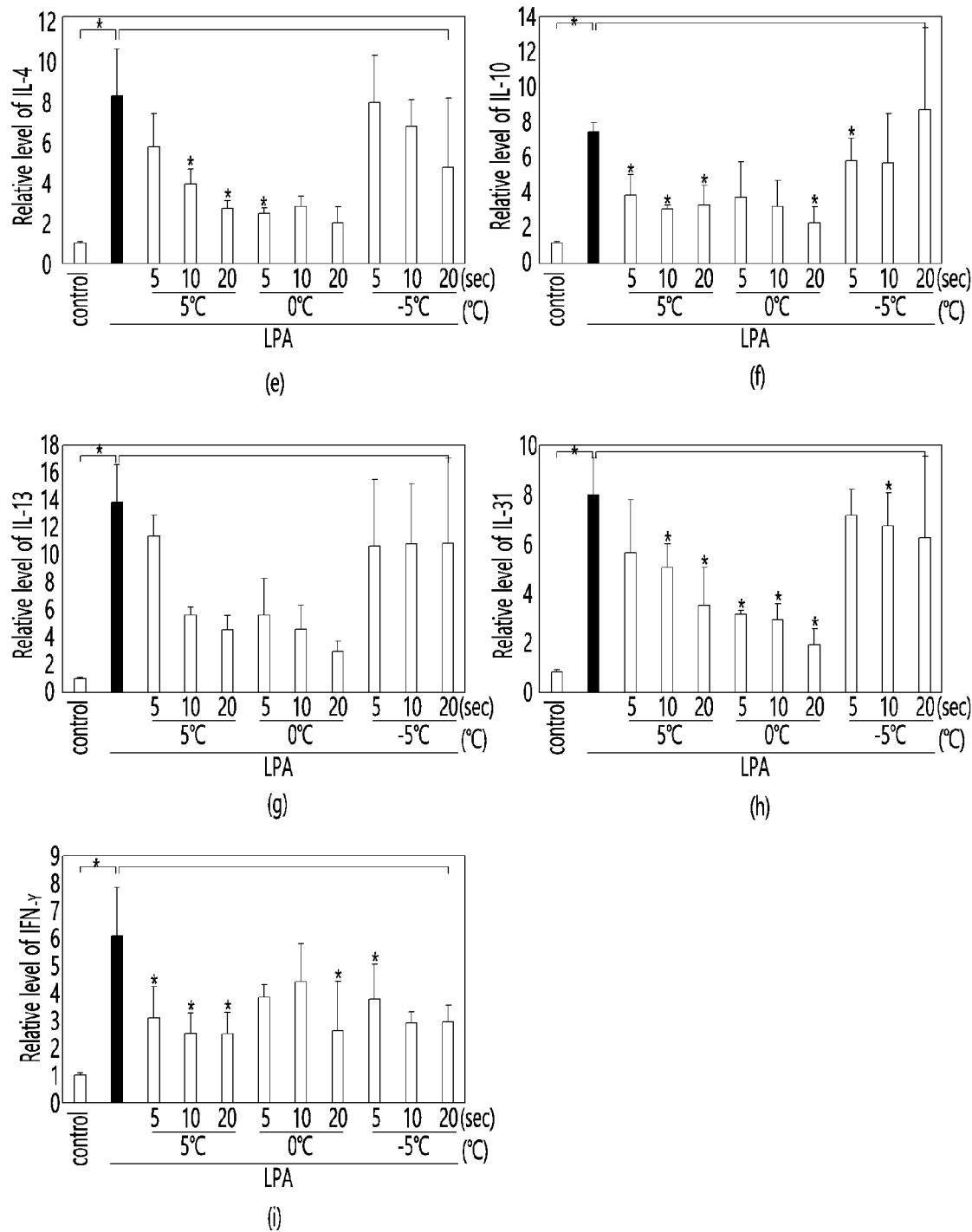

FIGS. 9 and 10 are graphs comparing gene expression levels of biomarkers related to itchiness. Specifically, the following were compared for each biomarker: the level of gene expression in the case of not injecting LPA, the level of gene expression in the case of LPA injection but no cooling treatment, and the level of gene expression after LPA injection and cooling treatment.

Referring to FIGS. 9 and 10, for most of the biomarkers, it was confirmed that the expression level in the case of LPA injection and cooling treatment tended to be lower than that in the case of LPA spraying without cooling treatment.

Referring to the graph a of FIG. 9, in the case of the TRPA1 gene, it can be seen that the expression level is significantly lower, especially when cooling treatment is performed ① at 5° C. for 5, 10 and 20 seconds, ② at 0° C. for 5, 10 and 20 seconds ③ at −5° C. for 5 seconds. Furthermore, it can be confirmed that the expression level of the TRPA1 gene was reduced to about 50% or less in the cooling treatment at 0° C.

Referring to the graph b of FIG. 9, in the case of the TRPV1 gene, it can be seen that the expression level is significantly low, especially when cooling treatment is performed ① at 5° C. for 5, 10, and 20 seconds, and ② at 0° C. for 5, 10, and 20 seconds. Furthermore, it can be confirmed that the expression level of the TRPV1 gene was reduced to about 60% or less in the cooling treatment at 0° C.

Referring to graph c of FIG. 9, in the case of the TRPM8 gene, it can be confirmed that the expression level is significantly low, especially when cooling treatment is performed ① at 5° C. for 10 and 20 seconds, and ② at 0° C. for 5, 10 and 20 seconds. Furthermore, it can be confirmed that the expression level of the TRPM8 gene was reduced to about 50% or less in the cooling treatment at 0° C.

Referring to the graph d of FIG. 9, in the case of the PAR2 gene, it can be seen that the expression level is significantly low, especially when cooling treatment is performed ① at 5° C. for 10 and 20 seconds, ② at 0° C. for 5, 10 and 20 seconds, and ③ at −5° C. for 5 seconds. Furthermore, it can be confirmed that the expression level of the TRPM8 gene was reduced to about 50% or less in the cooling treatment at 0° C. and 5° C.

Referring to the graph e of FIG. 10, in the case of the IL-4 gene, it can be seen that all expression levels were significantly low except for the case where the cooling treatment was performed at −5° C. for 5 seconds. In particular, it can be confirmed that the expression level of the IL-4 gene was reduced to about 50% or less in the cooling treatment at 5° C. for 10 seconds and 20 seconds, and in the cooling treatment at 0° C.

Referring to the graph f of FIG. 10, in the case of the IL-10 gene, it can be seen that all expression levels are significantly low, except for the case where 20 seconds of cooling treatment was performed at −5° C. In particular, it can be seen that the expression level of the IL-10 gene was reduced to about 50% or less in the cooling treatment at 0° C. and 5° C.

Referring to the graph g of FIG. 10, in the case of the IL-13 gene, it can be confirmed that the expression level is significantly low in all cooling treatments. In particular, it can be confirmed that the expression level of the IL-13 gene was reduced to about 50% or less in the cooling treatment at 5° C. for 10 seconds and 20 seconds, and in the cooling treatment at 0° C.

Referring to the graph h of FIG. 10, in the case of the IL-31 gene, it can be confirmed that the expression level is significantly low in all cooling treatments. In particular, it can be seen that the expression level of IL-31 gene decreased to about 50% or less in the cooling treatment at 5° C. for 20 seconds and in the cooling treatment at 0° C.

Referring to the graph i of FIG. 10, in the case of the IFN-γ gene, it can be confirmed that the expression level was significantly low in all cooling treatments. In particular, it can be confirmed that the expression level of the IFN-γ gene was reduced to about 50% or less in the cooling treatment at 5° C.

Figure 11:
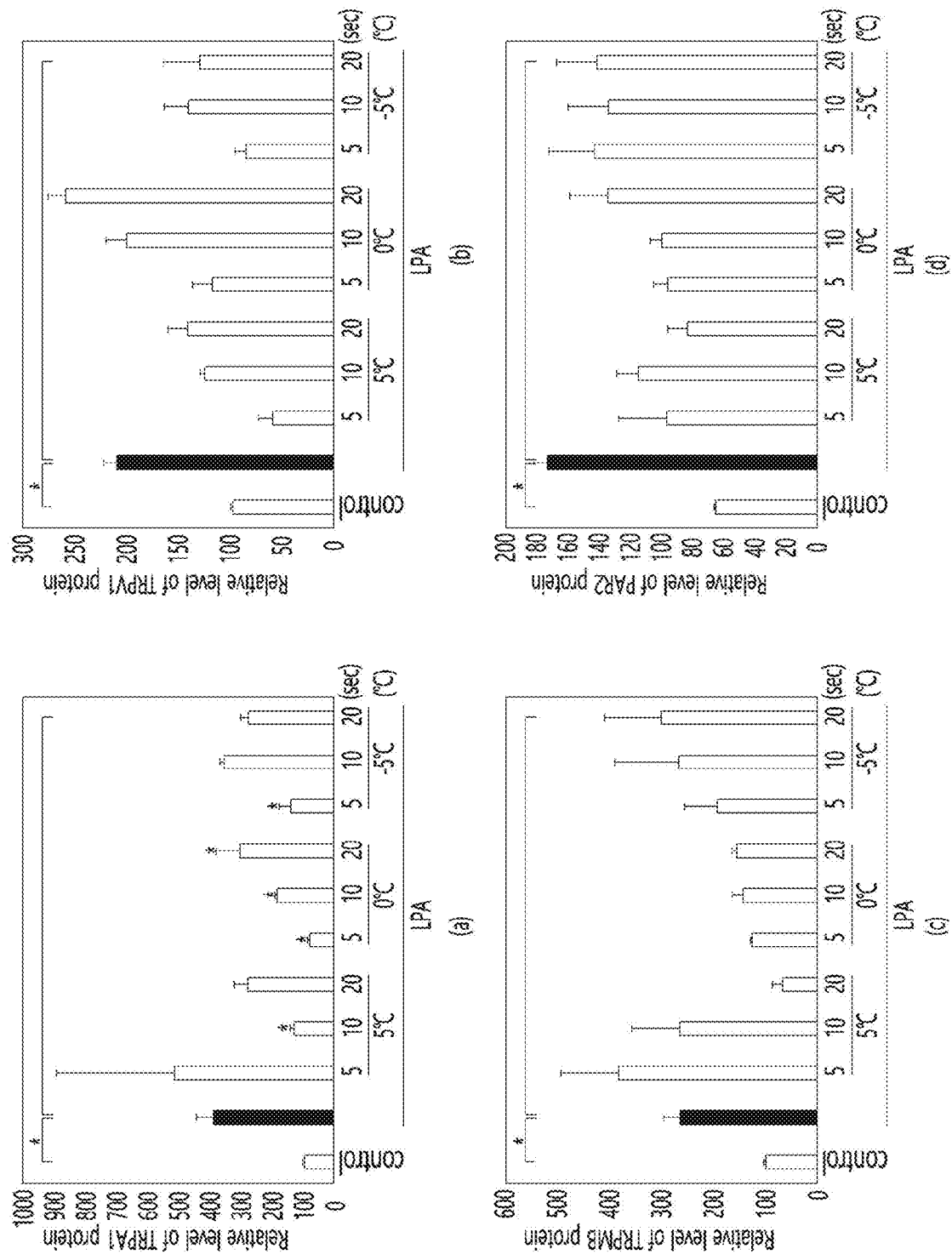
Figure 12:
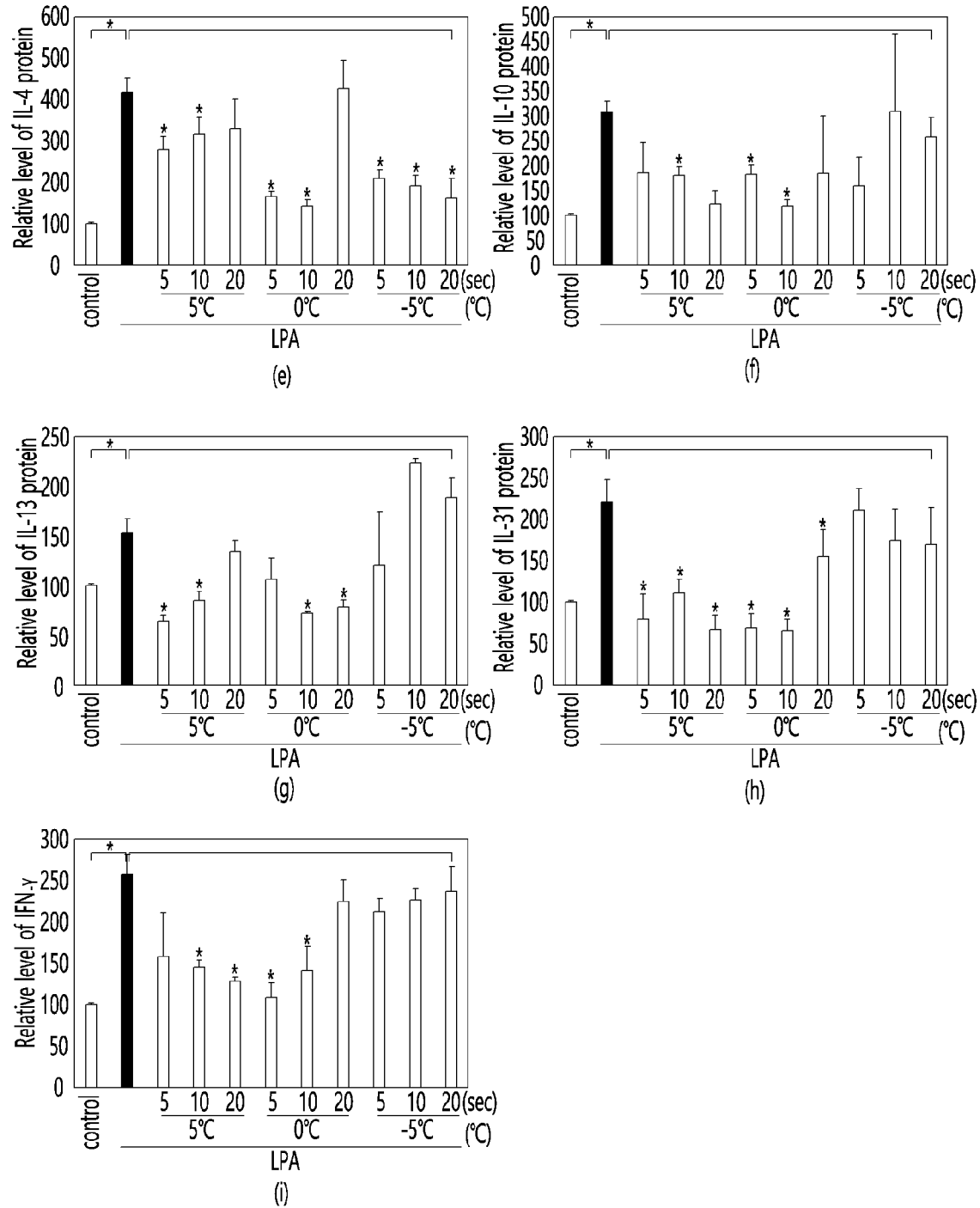

FIGS. 11 and 12 are graphs comparing protein expression levels of biomarkers related to itching. Specifically, for each biomarker the following were compared: the level of protein expression in the case of not injecting LPA, the protein expression level in the case of LPA spraying without cooling treatment, and the protein expression level after LPA spraying and cooling treatment.

Referring to FIG. 11, in most biomarkers, it was observed that the protein expression level when LPA was injected and cooling treatment was performed had a relatively lower value than when LPA was injected but cooling treatment was not performed.

Referring to the graph a of FIG. 11, in the case of the TRPA1 protein, it was confirmed that the expression level was significantly low when cooling treatment was performed ① at 5° C. for 10 and 20 seconds, ② at 0° C. for 5, 10 and 20 seconds ③ at −5° C. for 5, 10 and 20 seconds.

Referring to graph b of FIG. 11, in the case of the TRPV1 protein, it was confirmed that the expression level was significantly low when cooling treatment was performed ① at 5° C. for 5, 10, and 20 seconds, ② at 0° C. for 5 and 10 seconds, and ③ at −5° C. for 5, 10, and 20 seconds for cooling treatment. Further, it can be confirmed that the expression level of the TRPV1 protein was reduced to about 60% or less in the cooling treatments at 5° C. and −5° C.

Referring to graph c of FIG. 11, in the case of the TRPM8 protein, it was confirmed that the expression level was significantly low when cooling treatment was performed ① at 5° C. for 20 seconds, ② at 0° C. for 5, 10 and 20 seconds, and ③ at −5° C. for 5 seconds. Furthermore, it can be confirmed that the expression level of TRPM8 protein was reduced to about 50% or less in the cooling treatment at 0° C.

Referring to graph d of FIG. 11, in the case of PAR2 protein, it was confirmed that the expression level was significantly low when cooling treatment was performed ① at 5° C. for 5, 10 and 20 seconds, ② at 0° C. for 5, 10 and 20 seconds, and ③ at −5° C. for 5, 10 and 20 seconds. Furthermore, it can be confirmed that the expression level of PAR2 protein was reduced to about 70% or less in the cooling treatment at −5° C.

Referring to the graph e of FIG. 12, in the case of IL-4 protein, it can be seen that all expression levels were significantly low except for the case where the cooling treatment was performed at 0° C. for 20 seconds. In particular, it can be seen that the expression level of IL-4 protein decreased to about 50% or less in the cooling treatment at 0° C. for 5 seconds and 10 seconds and in the cooling treatment at −5° C.

Referring to the graph f of FIG. 12, in the case of the IL-10 protein, it can be seen that all expression levels were significantly low except for the case where 10 seconds of cooling treatment was performed at −5° C. In particular, it can be seen that the expression level of IL-10 protein was reduced to about 60% or less in the cooling treatment at 0° C. and 5° C.

Referring to the graph g of FIG. 12, in the case of the IL-13 protein, it was confirmed that the expression level was significantly low especially when cooling treatment was performed ① at 5° C. for 5, and 10 seconds, and ② at 0° C. for 5, 10, and 20 seconds.

Referring to graph h of FIG. 12, in the case of the IL-31 protein, it can be seen that all expression levels were significantly low except for the case where the cooling treatment was performed at −5° C. for 5 seconds. In particular, it can be seen that the expression level of IL-31 protein decreased to about 50% or less in the cooling treatment at 0° C. for 5 seconds and 10 seconds and in the cooling treatment at 5° C.

Referring to the graph i of FIG. 12, in the case of IFN-γ protein, it can be confirmed that the expression level was significantly low in all cooling treatments. In particular, it can be seen that the expression level of IFN-γ protein was reduced to about 60% or less in the cooling treatment at 0° C. for 5 seconds and 10 seconds and in the cooling treatment at 5° C.

Considering the results of the above analysis, it has been demonstrated that if cooling treatment is performed to relieve itching, cooling treatment to control the affected area suspected of itching to a specific temperature is capable of relieving the itching.

Furthermore, it has been demonstrated that itching can also be alleviated when the affected area suspected of itching is controlled to a specific temperature and maintained at a specific temperature for a specific time.

On the other hand, it can be quantitatively confirmed that the genes and proteins related to the induction of itching are relatively less expressed when the cooling treatment is performed at a specific temperature and for a specific time through the analysis result. In particular, when cooling is performed to an appropriate cooling temperature (for example, 0° C.), it is seen that the itching factor and atopic factor are generally further reduced than when the cooling temperature is low (for example, when cooling is performed at −5° C.) or when the cooling temperature is high (for example, when cooling to 5° C. is performed), showing that precise control of the cooling temperature is essential in that even a minute temperature difference affects the result.

Similarly, it can be seen that the result can vary depending on the cooling time to maintain the temperature of the affected area at a specific cooling temperature, so that performing cooling for the correct cooling time is also an essential control variable.

Figure 13:
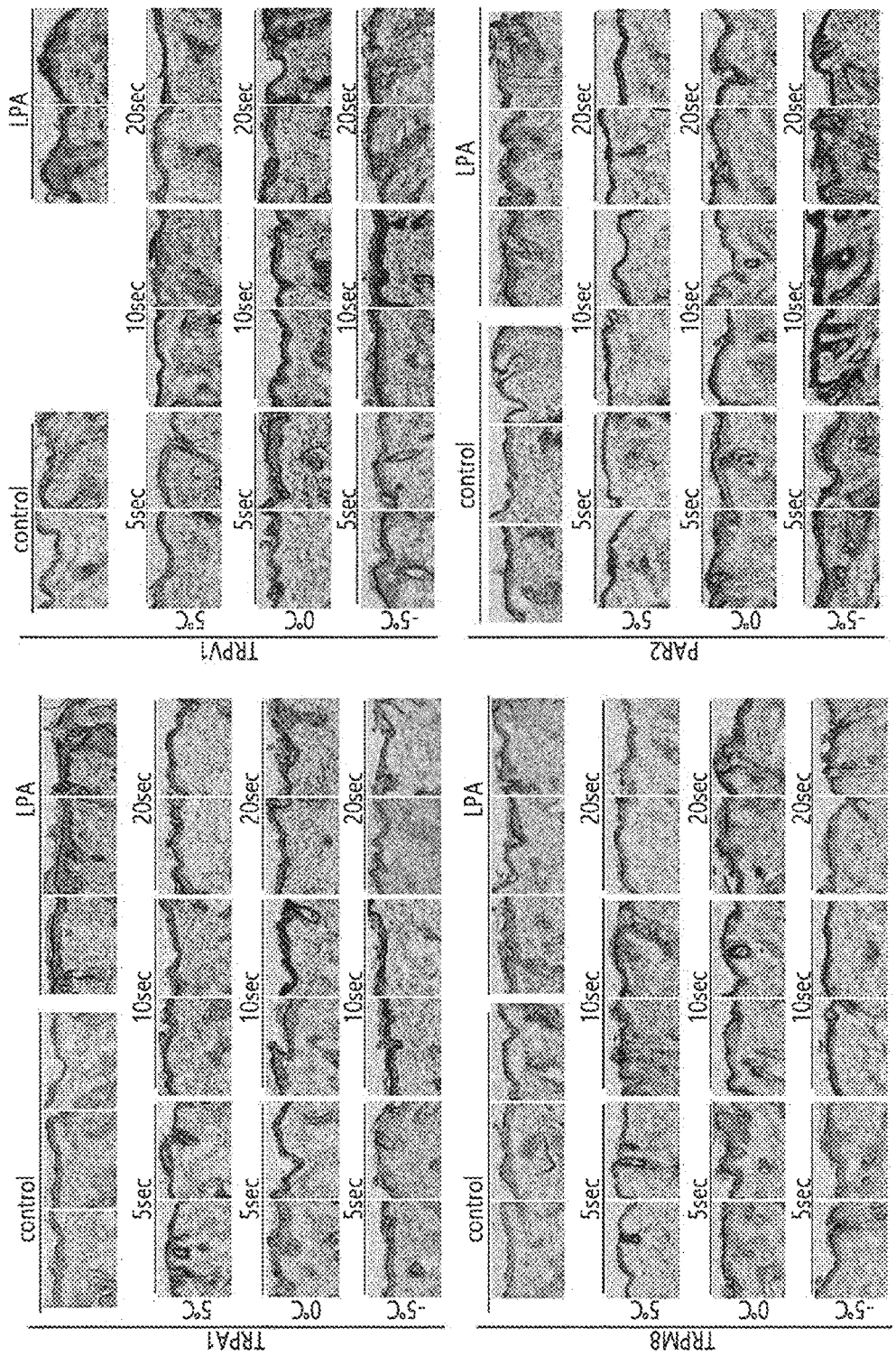
Figure 14:
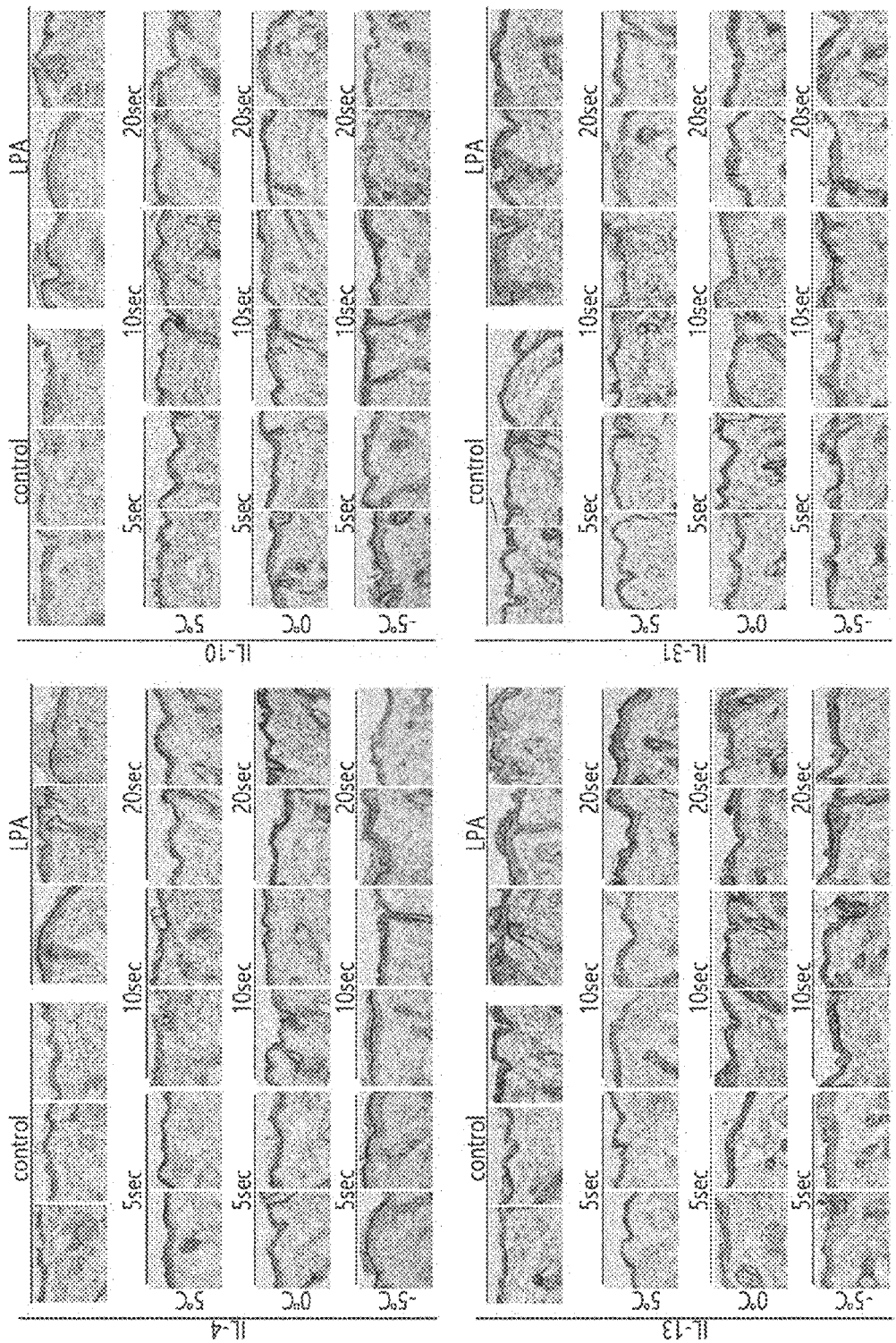
Figure 15:
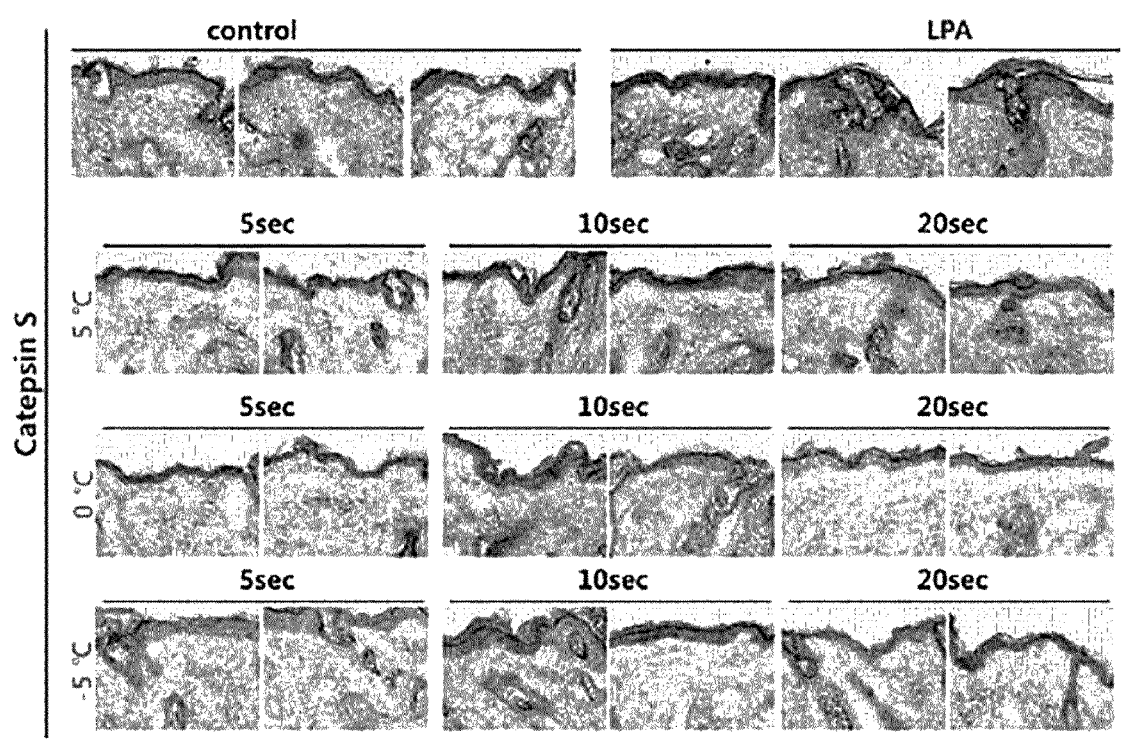

FIGS. 13 to 15 are diagrams showing the results of staining a tissue sample using an immunohistochemical method after performing a cooling treatment on the affected area.

As for the immunohistochemical method, as described above, after scarifying two mice per cooling condition, immunostaining was performed on the area to be cooled to observe histological changes. It can be seen that the broader and darker the staining, the more active the expression of the protein to be observed.

As a result of the analysis, referring to FIGS. 13 to 15, it was confirmed that the expression of biomarkers related to itching was observed relatively less in the case of LPA treatment and cooling treatment than in the case of LPA treatment and no cooling treatment.

In the case of TRPA1 protein, Cathepsin S protein, IL-4 protein, IL-10 protein, and IL-31 protein, the degree of staining was narrower and lighter in the case of cooling treatment than in the case of no cooling treatment under all conditions.

In the case of the TRPV1 protein, the degree of dyeing was narrower and lighter than that of the case without cooling treatment when cooling treatment was performed ① at 5° C. for 5 seconds and 20 seconds, ② at 0° C. for 5 seconds, and ③ at −5° C. for 5 sec, 10 sec, and 20 sec.

In the case of the PAR2 protein, the degree of dyeing was narrower and lighter than that of the case without cooling treatment when cooling treatment was performed ① at 5° C. for 5 seconds, 10 seconds, and 20 seconds, and ② at 0° C. for 5 seconds, 10 seconds and 20 seconds.

In the case of the IL-13 protein, the degree of dyeing was narrower and lighter than that of the case without cooling treatment when cooling treatment was performed ① at 5° C. for 5 seconds and 10 seconds, ② at 0° C. for 5 seconds, and ③ at −5° C. for 5 seconds and 10 seconds.

Through the above analysis results, it was visually confirmed that the protein related to the induction of itching was relatively less expressed when cooling treatment is performed at a specific temperature and for a specific time.

Therefore, it can be visually demonstrated that, if cooling treatment is performed to relieve itching, itching can be relieved by performing such treatment in order to maintain the affected area suspected of itching at a specific temperature.

4) Discussion

The cooling treatment method or the cooling processing method performed in the above-described experiment may comprise the following: a step of specifying the affected area as a target area; a step of setting the target temperature to −5° C., 0° C., or 5° C. and setting the cooling time to 5 seconds, 10 seconds, or 20 seconds; a step of disposing a cooling device relative to the target area; a step of operating a cooling device to spray a coolant on a target area, and applying thermal energy to the coolant using a temperature control means of the cooling device; a step of maintaining the temperature of the target area at the target temperature by measuring the temperature of the target area, so that if the measured temperature is lower than the set target temperature, the heat energy applied to the coolant per unit time is increased, and if the measured temperature is higher than the set target temperature, the thermal energy applied to the coolant per unit time is reduced; and a step of terminating the cooling treatment for the target area when the time during which the temperature of the target area is maintained at the target temperature is at least the set cooling time. In this case, in the step of maintaining the target area at the target temperature, this means that the temperature of the target area is maintained within a threshold range (for example, the threshold range is selected from 1° C. to 10° C.) at the target temperature.

Considering the experimental results, cooling treatment in which the affected area is maintained at −5° C., 0° C., or 5° C. for at least 5 seconds, 10 seconds, or 20 seconds can effectively relieve the itching of the affected area by reducing the expression of biomarkers related to itching.

Cooling treatment to maintain the affected area at 5° C. for 5 seconds may alleviate the itching of the affected area by reducing the expression of the TRPA1 gene, TRPV1 gene, PAR2 gene, IL-4 gene, IL-10 gene, IL-13 gene, IL-31 gene, IFN-γ gene, TRPV1 protein, PAR2 protein, IL-4 protein, IL-10 protein, IL-13 protein, IL-31 protein and IFN-γ protein.

Cooling treatment to maintain the affected area at 5° C. for 10 seconds may alleviate the itching of the affected area by reducing the expression of the TRPA1 gene, TRPV1 gene, TRPM8 gene, PAR2 gene, IL-4 gene, IL-10 gene, IL-13 gene, IL-31 gene, IFN-γ gene, TRPA1 protein, TRPV1 protein, PAR2 protein, IL-4 protein, IL-10 protein, IL-13 protein, IL-31 protein and IFN-γ protein.

Cooling treatment to maintain the affected area at 5° C. for 20 seconds may alleviate the itching of the affected area by reducing the expression of the TRPA1 gene, TRPV1 gene, TRPM8 gene, PAR2 gene, IL-4 gene, IL-10 gene, IL-13 gene, IL-31 gene, IFN-γ gene, TRPA1 protein, TRPV1 protein, TRPM8 protein, PAR2 protein, IL-4 protein, IL-10 protein, IL-13 protein, IL-31 protein, and IFN-γ protein.

Cooling treatment to maintain the affected area at 0° C. for 5 or 10 seconds may alleviate the itching of the affected area by reducing the expression of the TRPA1 gene, TRPV1 gene, TRPM8 gene, PAR2 gene, IL-4 gene, IL-10 gene, IL-13 gene, IL-31 gene, IFN-γ gene, TRPA1 protein, TRPV1 protein, TRPM8 protein, PAR2 protein, IL-4 protein, IL-10 protein, IL-13 protein, IL-31 protein, and IFN-γ protein.

Cooling treatment to maintain the affected area at 0° C. for 20 seconds may alleviate the itching of the affected area by reducing the expression of the TRPA1 gene, TRPV1 gene, TRPM8 gene, PAR2 gene, IL-4 gene, IL-10 gene, IL-13 gene, IL-31 gene, IFN-γ gene, TRPA1 protein, TRPM8 protein, PAR2 protein, IL-10 protein, IL-13 protein, IL-31 protein, and IFN-γ protein.

Cooling treatment to maintain the affected area at −5° C. for 5 seconds may alleviate the itching of the affected area by reducing the expression of the PAR2 gene, IL-10 gene, IL-13 gene, IL-31 gene, IFN-γ gene, TRPA1 protein, TRPV1 protein, TRPM8 protein, PAR2 protein, IL-4 protein, IL-10 protein, IL-13 protein, IL-31 protein, and IFN-γ protein.

Cooling treatment to maintain the affected area at −5° C. for 10 seconds may alleviate the itching of the affected area by reducing the expression of the IL-4 gene, IL-10 gene, IL-13 gene, IL-31 gene, IFN-γ gene, TRPA1 protein, TRPV1 protein, PAR2 protein, IL-4 protein, IL-31 protein, and IFN-γ protein.

Cooling treatment to maintain the affected area at −5° C. for 20 seconds may alleviate the itching of the affected area by reducing the expression of the IL-4 gene, IL-13 gene, IL-31 gene, IFN-γ gene, TRPA1 protein, TRPV1 protein, PAR2 protein, IL-4 protein, IL-10 protein, IL-31 protein, and IFN-γ protein As mentioned above, in animal experiments, the set target temperatures of 5° C., 0° C., and −5° C. and the set cooling time of 5 sec, 10 sec, and 20 sec are critical in that they inhibit the expression of a number of biomarkers related to itching. In other words, in the cooling treatment method for skin diseases using precision cooling technology, if the temperature of the target area is maintained at the target temperature for a cooling time, the target temperature is selected from −5° C. to 5° C., and the cooling time is selected from 5 seconds to 20 seconds, it can be understood that it has a remarkable effect of alleviating itching in the target area.

In particular, preferably, if the target temperature is selected from 0° C. to 5° C. and the cooling time is selected from 5 to 20 seconds, the expression of both the IL-31 gene and protein, which are known to be correlated with chronic itching, is effectively suppressed, resulting in a higher itching relief effect. More preferably, by selecting the target temperature as 0° C. and the cooling time as 20 seconds, the expression of all of the above-described itch-related biomarkers is reduced to a low level, so that a high itching alleviation effect can occur.

2. Inflammatory Acne

Hereinafter, an animal experiment to prove the effect of alleviating inflammatory acne symptoms through the cooling treatment method using the above-described precision cooling technology will be described in detail. As will be described later, with the cooling treatment method using precision cooling technology it is possible to reduce the expression of biomarkers associated with inflammatory acne in the target area performing cooling and also reduce the size of inflammatory acne; accordingly, it can be proven that the cooling treatment method using precision cooling technology relieves the symptoms of inflammatory acne.

Additionally, based on the results of animal experiments to be described later, in reducing the expression of biomarkers in the target area through a cooling treatment method using precision cooling technology, the critical significance of the target temperature for cooling the target area and the critical significance of the cooling time for maintaining the temperature of the target area at the target temperature will also be described.

(1) Animal Experimentation

According to the results of animal experimentation analysis to be described later, in performing cooling treatment for inflammatory acne symptoms, the target temperature and/or cooling time are factors that greatly affect the alleviation effect of inflammatory acne symptoms.

Therefore, in order to generate a therapeutic effect of inflammatory acne, the target temperature for cooling the target area and/or the cooling time for maintaining the temperature of the target area at the target temperature must be very finely controlled. The present specification is meaningful in that an optimal target temperature and/or cooling time was found to alleviate the symptoms of inflammatory acne.

Hereinafter, in relation to the method of treating inflammatory acne according to an embodiment of the present specification, the target temperature and/or cooling time at which the therapeutic effect is significantly increased will be described in detail.

1) Experimental Example

Hereinafter, an experimental example for demonstrating the effect of a treatment method for alleviating inflammatory acne symptoms by cooling a target area according to an embodiment of the present specification will be described in detail with reference to FIGS. 16 to 25. Through the experimental results to be described later, it is confirmed that the alleviation effect of inflammatory acne symptoms occurs when cooling treatment is performed on a target area at a specific target temperature and a specific cooling time according to the treatment method for inflammatory acne according to an embodiment of the present specification.

In this experimental example, in order to treat Cutibacterium acnes (hereinafter, C. acnes)-induced inflammatory acne in mice, a cooling device (Recensmedical, Cryo-VIVE, Korea) capable of controlling temperature and time was used to cool the area related to inflammatory acne. Specifically, the cooling device used the above-described spray-type cooling device, and cooling treatment was performed by spraying a coolant for inflammatory acne.

In addition, in this experimental example, the size of the inflammatory acne lesion before and after the cooling treatment was investigated.

Further, in this experimental example, using real-time polymerase chain reaction (PCR) and immunohistochemistry, the expression level of the following biomarkers before and after cooling treatment was investigated.

Interleukin (IL)-1α (Qiagen, Mm-IL-1α-SG),
IL-1β (Qiagen, Mm-IL-1β-SG),
Il-6 (1:200 dilution; Abcam),
Il-8 (1:200 dilution; Abcam),
Tumor necrosis factor (TNF)-α (1:200 dilution; R and D)
Matrix metalloproteinase (MMP)-1 (1:200 dilution; Abcam),
MMP-3 (1:200 dilution; Abcam),
MMP-9 (1:250 dilution; Abcam,), The above-mentioned biomarkers are biomarkers related to inflammatory acne or skin regeneration, which are related to inflammatory cytokines and dermal decomposition matrix, and are factors that have a tendency to increase in inflammatory acne. Here, MMP-1, MMP-3, and MMP-9 are matrix metalloproteinases that, when activated, promote the breakdown of connective tissue in the dermis and that tend to be increased by multiple times in inflammatory acne patients as compared to normal people. Therefore, suppression of gene or protein expression of the above-mentioned biomarkers results in demonstrating the therapeutic effect of inflammatory acne.

Figure 16:
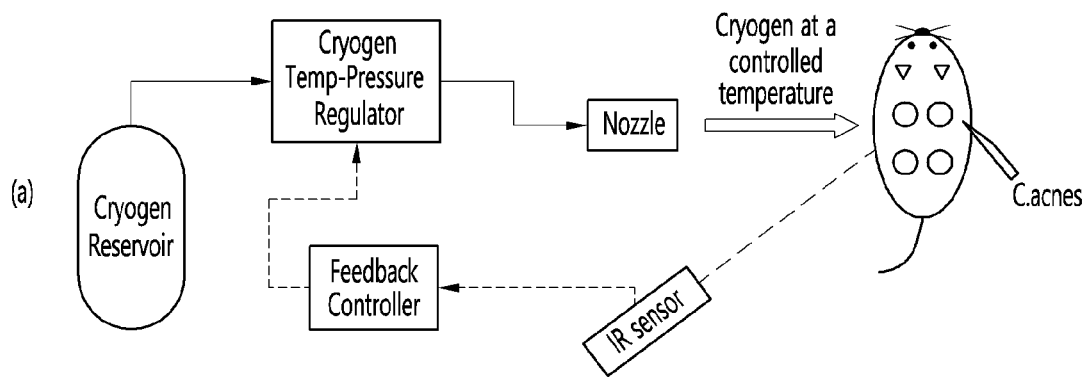
FIG. 16 is a diagram showing an animal experiment design for confirming the degree of suppression of the expression of related biomarkers according to the cooling treatment for inflammatory acne according to an embodiment of the present specification.
Figure 16:
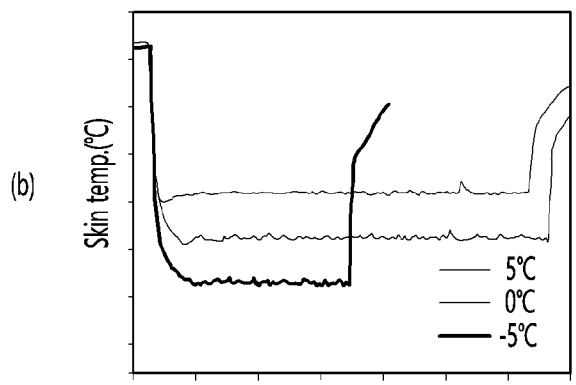
Figure 16:
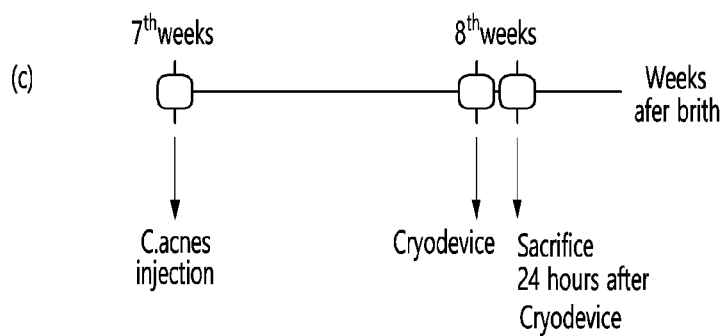

FIG. 16 is a view showing an animal experiment design for confirming the degree of suppression of the expression of related biomarkers according to the cooling treatment for inflammatory acne according to an embodiment of the present specification.

FIG. 16 (a) is a diagram briefly showing the cooling treatment system applied in the experiment. Referring to FIG. 16 (a), it can be seen the spray location of the C. acnes spray solution on the skin surface of the mice. FIG. 16 (b) is a graph showing an aspect in which the temperature of the target area is controlled by the cooling treatment system; FIG. 16 (c) is a schematic diagram of the experimental protocol. Hereinafter, the experimental process will be described in detail.

First, C. acnes was collected and identified after culturing using brain heart infusion agar under anaerobic conditions at 37° C. After centrifugation at 5000λ for 10 minutes, washing three times with phosphate buffered saline, 109 colony forming units (CFU)/20 μl concentration of C. acnes spray solution was prepared.

Then, 6-week-old female HR-1 mice (HR-1; SLC Inc., Hamamatsu, Japan) were acclimatized to the cage for 1 week. C. acnes spray solution prepared at a concentration of 109 colony forming units (CFU)/20 μl was intradermally injected into 4 sites (see FIG. 11) per mouse using a 30-gauge syringe. At one week after spraying of the C. acnes injection solution, a cooling treatment was performed on the above four sites using a cooling device. Specifically, cooling treatment was performed of the C. acnes spray solution to each of the 4 sites of the sprayed mice as follows: ① at −20° C. temperature for 5 seconds, 10 seconds and 20 seconds; ② at −10° C. temperature for 5 seconds, 10 seconds and 20 seconds; ③ at −5° C. temperature for 5 seconds, 10 seconds and 20 seconds; ④ at 0° C. temperature for 5 seconds, 10 seconds and 20 seconds; and ⑤ at 5° C. temperature for 5 seconds, 10 seconds and 20 seconds.

At this time, cooling treatment was performed on two mice under the same conditions for each cooling condition. The cooling treatment used a cooling device developed and provided by RecensMedical Inc. Specifically, heat was applied to the cryogenic material (e.g., carbon dioxide) to control the thermodynamic state (e.g., temperature and/or pressure) of the cryogenic material, and the cryogenic material was stayed onto the area sprayed with the C. acnes spray solution that is, the acne-related affected area. In addition, the IR sensor measures the temperature of the affected area in real time, and performs feedback control based on the difference between the preset cooling target temperature and the real-time measured temperature; therefore, the heat applied to the cryogenic material was adjusted to maintain the temperature of the affected area at a preset cooling target temperature. Through this, the cooling treatment was performed while precisely controlling the temperature of the affected area within the target temperature to be cooled.

On the other hand, in order to compare the effect of the cooling treatment, a group of mice injected with the C. acnes injection solution but not subjected to cooling treatment, and a group not injected with the C. acnes injection solution, were prepared as control groups.

In addition, at a time point about a week after the C. acnes injection solution was injected, each mouse was scarified. RNA was isolated, and size analysis of the acne lesions, acne gene expression analysis, and immunohistostaining analysis, which will be described later, were performed.

2) Method of Analysis a. Size Analysis of Inflammatory Lesions

After the cooling treatment for 5 seconds, 10 seconds, or 20 seconds of the group (hereinafter, Group 1) subjected to the cooling treatment with respect to the mice injected with the C. acnes injection solution, the size of the lesion for all four sites was measured. The size of the lesions in all four sites at the same time point was also measured for the group (hereinafter, Group 2) to which the cooling treatment was not performed on the mice that were infused with C. acnes injection solution.

Since the cooling treatment was performed on 2 mice per cooling condition, the average value of the size of the lesion measured at a total of 8 sites was calculated.

b. Immunohistochemical Analysis

Tissue samples associated with inflammatory acne were obtained from each mouse and placed in a cryomold with embedding medium. Tissue samples were frozen at −80° C., cut to a thickness of 7 μm, and fixed with 4% paraformaldehyde and 0.1% Triton X-100 for 10 minutes. After 1 hour treatment with 5% normal donkey serum (Jackson ImmunoResearch), incubation was performed overnight at 4° C. with antibodies against the following target proteins of observation: (Interleukin (IL)-1β (1:200 dilution; Abcam), Il-6 (1:200 dilution; Abcam), Il-8 (1:200 dilution; Abcam), Tumor necrosis factor (TNF)-α (1:200 dilution; R and D), Matrix metalloproteinase (MMP)-1 (1:200 dilution; Abcam), MMP-3 (1:200 dilution; Abcam), MMP-9 (1:250 dilution; Abcam)).

Thereafter, the tissue samples were washed three times with phosphate-buffered saline, a secondary antibody conjugated with horseradish peroxidase (HRP) was added, and incubated at room temperature for 1 hour.

At this time, 3-amino9-ethylcarbazole (DAKO, Glostrup, Denmark) was used as a color developing reagent for horseradish peroxidase (HRP). In addition, slides were counterstained with hematoxylin. The above-described procedures were performed in duplicate.

c. Observation of Lesion Thickness

Additionally, as described above, after obtaining C. acnes-infused and cooling-treated lesion tissue sections from two mice for each cooling condition, tissue sections were subjected to H&E staining (Hematoxylin and Eosin Stain) to observe the thickness of the lesion.

d. Real-Time PCR Analysis

Total RNA was isolated from the isolated RNA using TRIzol reagent and stored in a 1.5 mL tube. Then, 0.1 volume of 1-bromo-3-chloropropane was added to the tube, vortexed for 1 minute, and cooled with ice for 10 minutes. Thereafter, centrifugation was performed at 4° C. and 12,000 rpm for 30 minutes, and the supernatant was separated into a new tube.

After adding the same volume of isopropanol to the separated supernatant, it was left at −20° C. for 2 hours or more. Thereafter, the supernatant was removed by centrifugation at 4° C. and 12,000 rpm for 30 minutes to obtain an RNA pellet.

Again, 1 ml of 75% ethanol was added, and the supernatant was discarded by centrifugation at 4° C. and 12,000 rpm for 15 minutes to additionally obtain an RNA pellet. The obtained RNA pellet was dissolved in an appropriate amount of DEPC-water and the concentration was measured.

Thereafter, cDNA was synthesized from 3 mg of total RNA using a cDNA synthesis kit (Promega, Madison, WI, USA) comprising ImProm-II™ reverse transcriptase and oligo-dT primers.

50 ng of synthesized cDNA; 10 pM of specific oligonucleotide primers for IL-1α, IL-1β, IL-6, IL-8, TNF-α, MMP-1, MMP-3 and MMP-9; and Power SYBR Green premix (Applied Bio-systems, Foster City, CA, USA) were used to perform Real-time PCR in duplicate.

The PCR primers used for PCR analysis are as follows:

| Gene | Direction | Sequence |
|---|---|---|
| Mouse IL-6 | Forward | 5'-ACCACTTCACAAGTCGGAGG-3' |
| | Reverse | 5'-TGCAAGTGCATCATCGTTGTTC-3' |
| TNF-α | Forward | 5'-GGCAGGTCTACTTTGGAGTCATTG-3' |
| | Reverse | 5'-ACATTCGAGGCTCCAGTGAATTCGG-3' |
| MMP-1 | Forward | 5'-TGAACATCCATCCCGTGACC-3' |
| | Reverse | 5'-GCGCTCAGTCTCTTCACCTC-3' |
| MMP-3 | Forward | 5'-TCCCTGCAACCGTGAAGAAG-3' |
| | Reverse | 5'-ACACCTGGAAAGTCCTCAGC-3' |
| MMP-9 | Forward | 5'-ACGACATAGACGGCATCCAG-3' |
| | Reverse | 5'-GGACACATAGTGGGAGGTGC-3' |

Cycling conditions for amplification were performed as follows:

Amplification was performed for 10 min at 95° C., 40 cycles for 15 s at 95° C., and 60 s at 60° C.

PCR products were evaluated with the Step one Plus (Applied Biosystems), a real-time PCR analysis software.

Statistical analysis of each analysis result was performed using SPSS version 18.0 (SPSS, Inc., Chicago, IL, USA).

In addition, repeated ANOVA was performed for each analysis result.

3) Analysis Result

Figure 17:
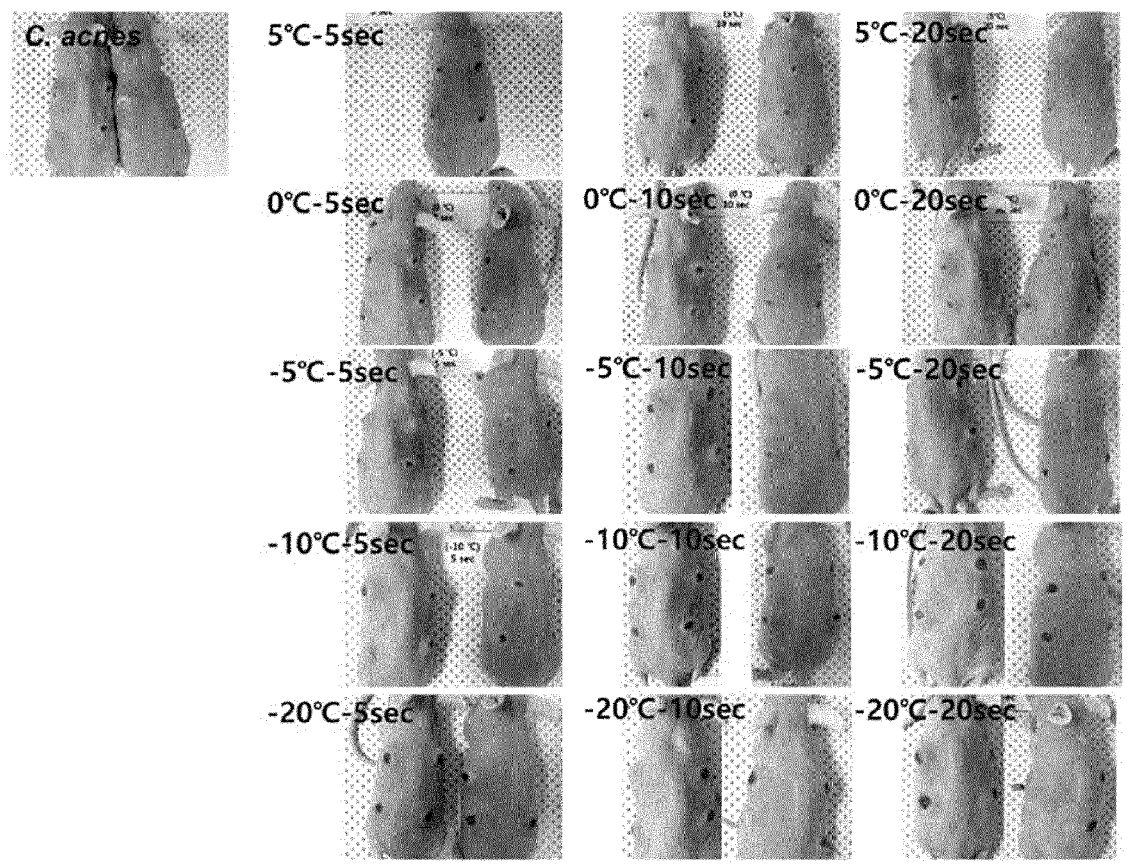
FIGS. 17 to 26 are diagrams showing the results of animal experiments on inflammatory acne.

FIG. 17 is a diagram illustrating the size of an inflammatory acne lesion. Specifically, FIG. 17 indicates, at each cooling condition, mice infused with C. acnes injection solution in Group 1 subjected to cooling treatment (on the right in each photo) and mice infused with C. acnes injection solution in Group 2 without cooling treatment (on the left in each photo).

Figure 18:
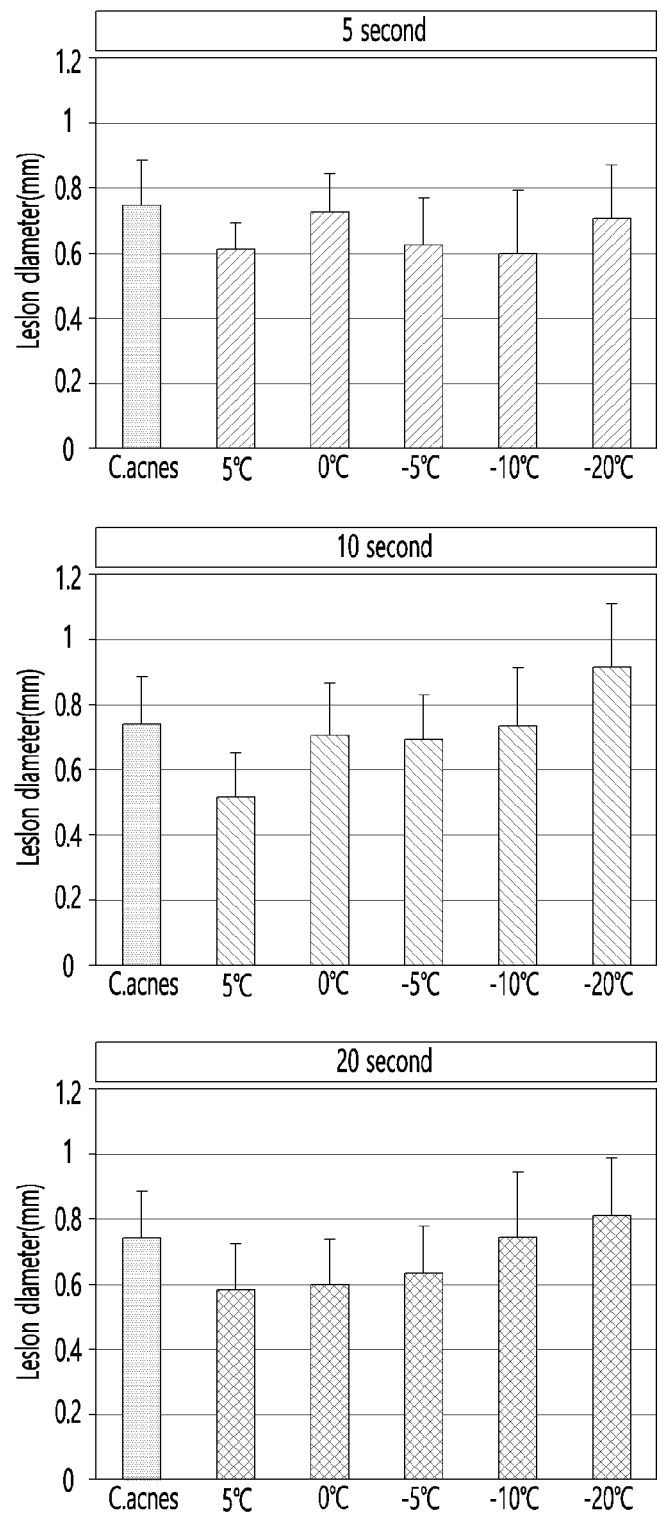

FIG. 18 is a graph comparing and analyzing the size of inflammatory acne lesions. Specifically, FIG. 18 shows a graph of calculating the size of the inflammatory acne lesion respectively when cooling treatment is performed for 5 seconds, when cooling treatment is performed for 10 seconds, and when cooling treatment is performed for 20 seconds.

Referring to FIGS. 17 and 18, for every timing of 5 seconds, 10 seconds and 20 seconds, it was observed that the size of the inflammatory acne lesion in Group 1, in which inflammatory acne was induced and cooling treatment was performed, tended to be smaller than that of Group 2 in which inflammatory acne was induced but not subjected to cooling treatment.

Specifically, when cooling was performed for 5 seconds, it was confirmed that the size of the lesion was relatively small in all cases of cooling to −20° C., −10° C., −5° C., 0° C., or 5° C. In particular, it was confirmed that the size of the inflammatory acne lesion was significantly reduced when cooling was performed at a temperature of −10° C., −5° C., 0° C., or 5° C.

When cooling was performed for 10 seconds, it was confirmed that the size of the lesion was relatively small when cooling was performed at a temperature of −10° C., −5° C., 0° C., or 5° C. In particular, it was confirmed that the size of the lesion of inflammatory acne was significantly reduced when cooling was performed at a temperature of −5° C., 0° C., or 5° C.

When cooling was performed for 20 seconds, it was confirmed that the size of the lesion was relatively small when cooling was performed at a temperature of −10° C., −5° C., 0° C., or 5° C. In particular, it was confirmed that the size of the lesion of inflammatory acne was significantly reduced when cooling was performed at a temperature of −5° C., 0° C., or 5° C.

Through this analysis result, it was confirmed that the size of the inflammatory acne lesion was reduced when cooling treatment was performed at a specific temperature and for a specific time. That is, it was confirmed that the inflammatory acne lesions were relatively relieved.

Therefore, in the case of performing cooling treatment to treat inflammatory acne, it can be demonstrated that inflammatory acne can be alleviated by performing cooling treatment to control the lesions associated with inflammatory acne to a specific temperature.

In addition, when cooling treatment is performed to treat inflammatory acne, it can be demonstrated that inflammatory acne can be alleviated by performing cooling treatment for a specific time while controlling the affected area associated with inflammatory acne to a specific temperature.

Figure 19:
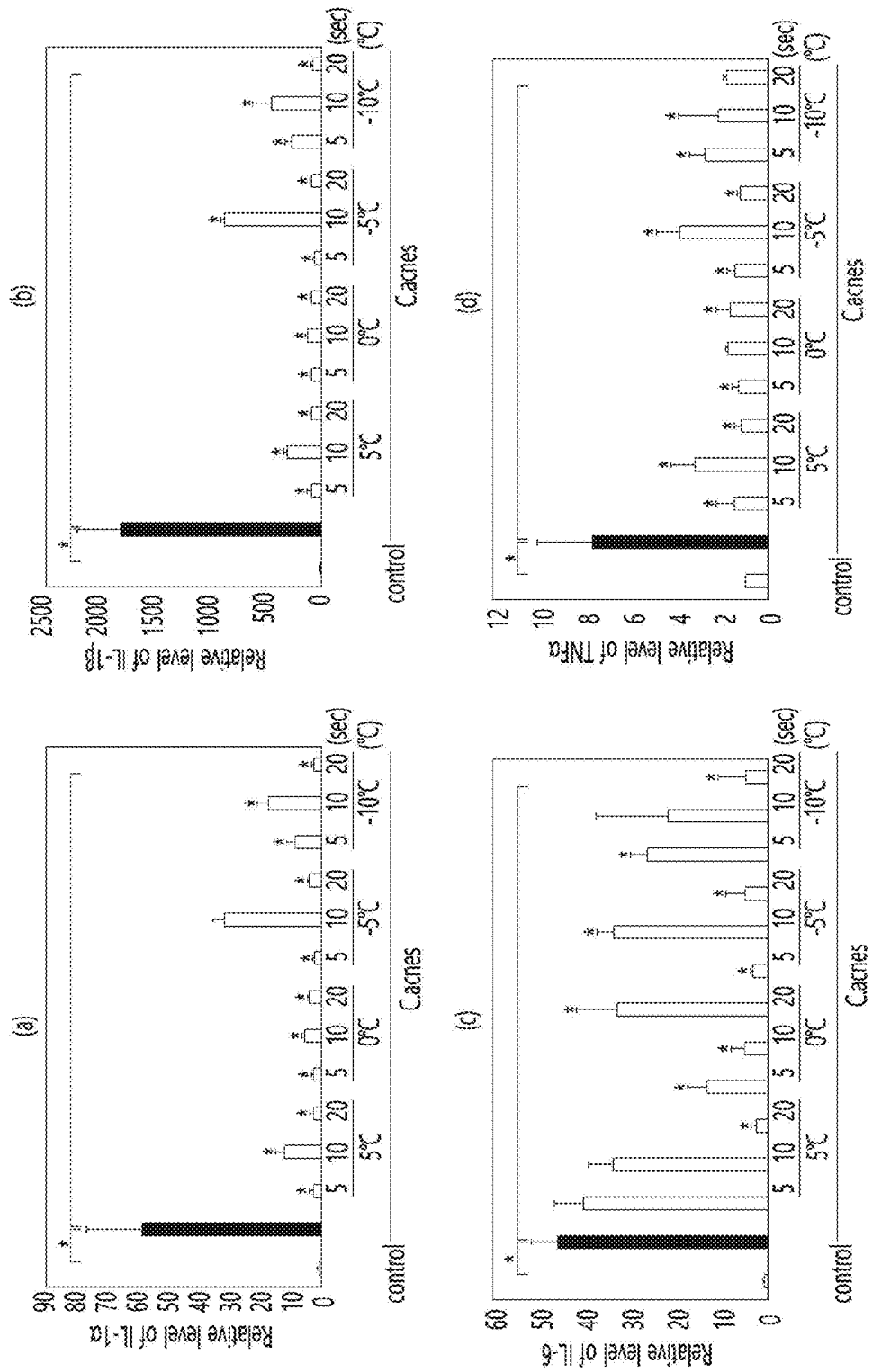
Figure 20:
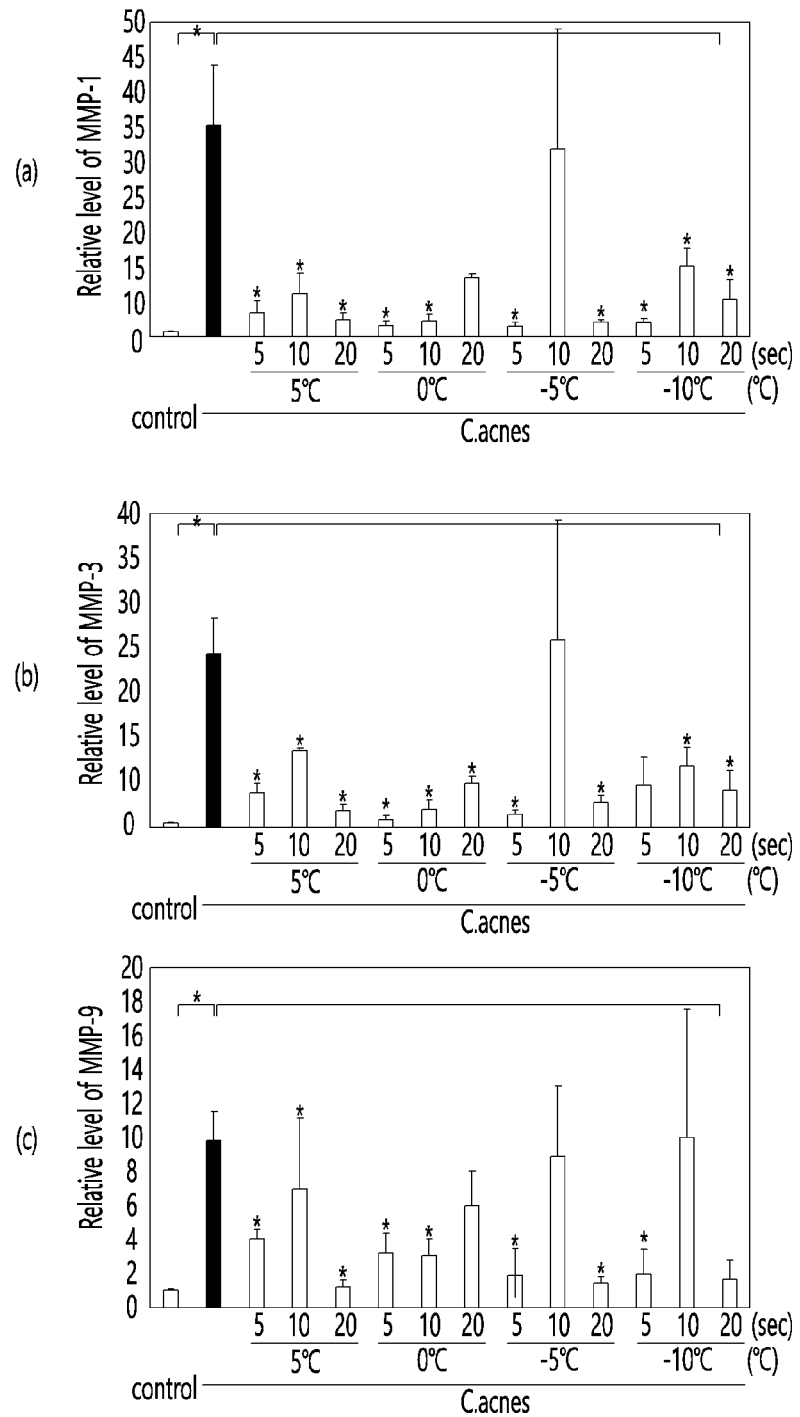

FIGS. 19 and 20 show graphs comparing and analyzing the expression level of gene biomarkers related to inflammatory acne, and the like; expression levels of gene biomarkers related to inflammatory acne in Group 1 to which the cooling treatment was performed and Group 2 to which the cooling treatment was not performed were compared and analyzed.

Referring to FIGS. 19 and 20, it was confirmed that the biomarkers related to inflammatory acne and the like tended to be expressed relatively less as follows in the case of Group 1, which was treated with cooling, than the case of Group 2, which was not treated with cooling.

Referring to graph a of FIG. 19, in the case of IL1-α, it was confirmed that the expression level was remarkably lower when cooling treatment was performed as follows: ① at 5° C. for 5, 10 and 20 seconds; ② at 0° C. for 5, 10 and 20 seconds; ③ at −5° C. for 5, 10 and 20 seconds; and ④ at −10° C. for 5, 10 and 20 seconds.

Referring to graph b of FIG. 19, in the case of IL1-β, it was confirmed that the expression level was remarkably lower when cooling treatment was performed as follows: ① at 5° C. for 5, 10 and 20 seconds; ② at 0° C. for 5, 10 and 20 seconds; ③ at −5° C. for 5, 10 and 20 seconds; and ④ at −10° C. for 5, 10 and 20 seconds.

Referring to graph c of FIG. 19, in the case of IL-6, it was confirmed that the expression level was remarkably lower when cooling treatment was performed as follows: ① at 5° C. for 5, 10 and 20 seconds; ② at 0° C. for 5, 10 and 20 seconds; ③ at −5° C. for 5, 10 and 20 seconds; and ④ at −10° C. for 5, 10 and 20 seconds.

Referring to graph d of FIG. 19, in the case of TNF-α, it was confirmed that the expression level was remarkably lower when cooling treatment was performed as follows: ① at 5° C. for 5, 10 and 20 seconds; ② at 0° C. for 5, 10 and 20 seconds; ③ at −5° C. for 5, 10 and 20 seconds; and ④ at −10° C. for 5, 10 and 20 seconds.

Referring to graph a of FIG. 20, in the case of MMP 1, it was confirmed that the expression level was remarkably lower when cooling treatment was performed as follows: ① at 5° C. for 5, 10 and 20 seconds; ② at 0° C. for 5, 10 and 20 seconds; ③ at −5° C. for 5 and 20 seconds (however, in the case of 10 seconds at −5° C., the expression level was significantly lower); and ④ at −10° C. for 5, 10 and 20 seconds.

Referring to graph b of FIG. 20, in the case of the biomarker of MMP3, it was confirmed that the expression level was remarkably lower when cooling treatment was performed as follows: ① at 5° C. for 5, 10 and 20 seconds; ② at 0° C. for 5, 10 and 20 seconds; ③ at −5° C. for 5 and 20 seconds; and ④ at −10° C. for 5, 10 and 20 seconds.

Referring to graph c of FIG. 20, in the case of the biomarker of MMP9, it was confirmed that the expression level was remarkably lower when cooling treatment was performed as follows: ① at 5° C. for 5, 10 and 20 seconds; ② at 0° C. for 5, 10 and 20 seconds; ③ at −5° C. for 5 and 20 seconds; and ④ at −10° C. for 5 and 20 seconds. It can be confirmed that the expression level is significantly lower than that in the case where cooling treatment is not performed even when cooling treatment is performed for 10 seconds at −5° C. or −10° C.

Through this analysis result, when cooling treatment was performed at a specific temperature and for a specific time, it was confirmed that the biomarkers (IL-1α, IL-1β, Il-6, TNF-α, MMP1, MJMP3, MMP9) related to inflammatory acne were relatively less expressed.

Therefore, in the case of performing cooling treatment to treat inflammatory acne, it can be demonstrated that inflammatory acne can be alleviated by performing cooling treatment to control the affected part associated with inflammatory acne to a specific temperature.

In addition, in the case of performing cooling treatment to treat inflammatory acne, it can be demonstrated that inflammatory acne can be alleviated by performing cooling treatment for a specific time while controlling the affected area associated with inflammatory acne to a specific temperature.

Figure 21:
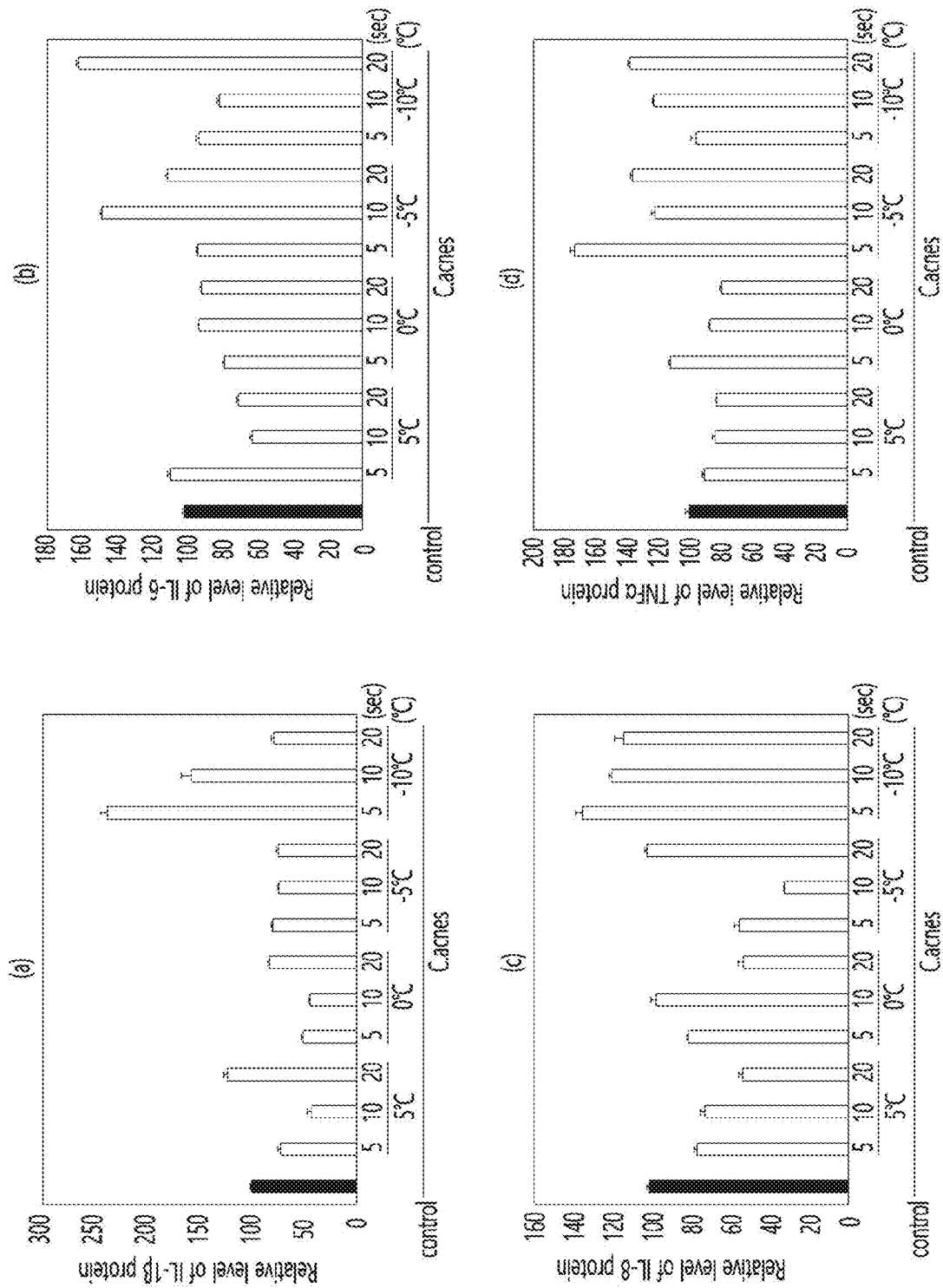
Figure 22:
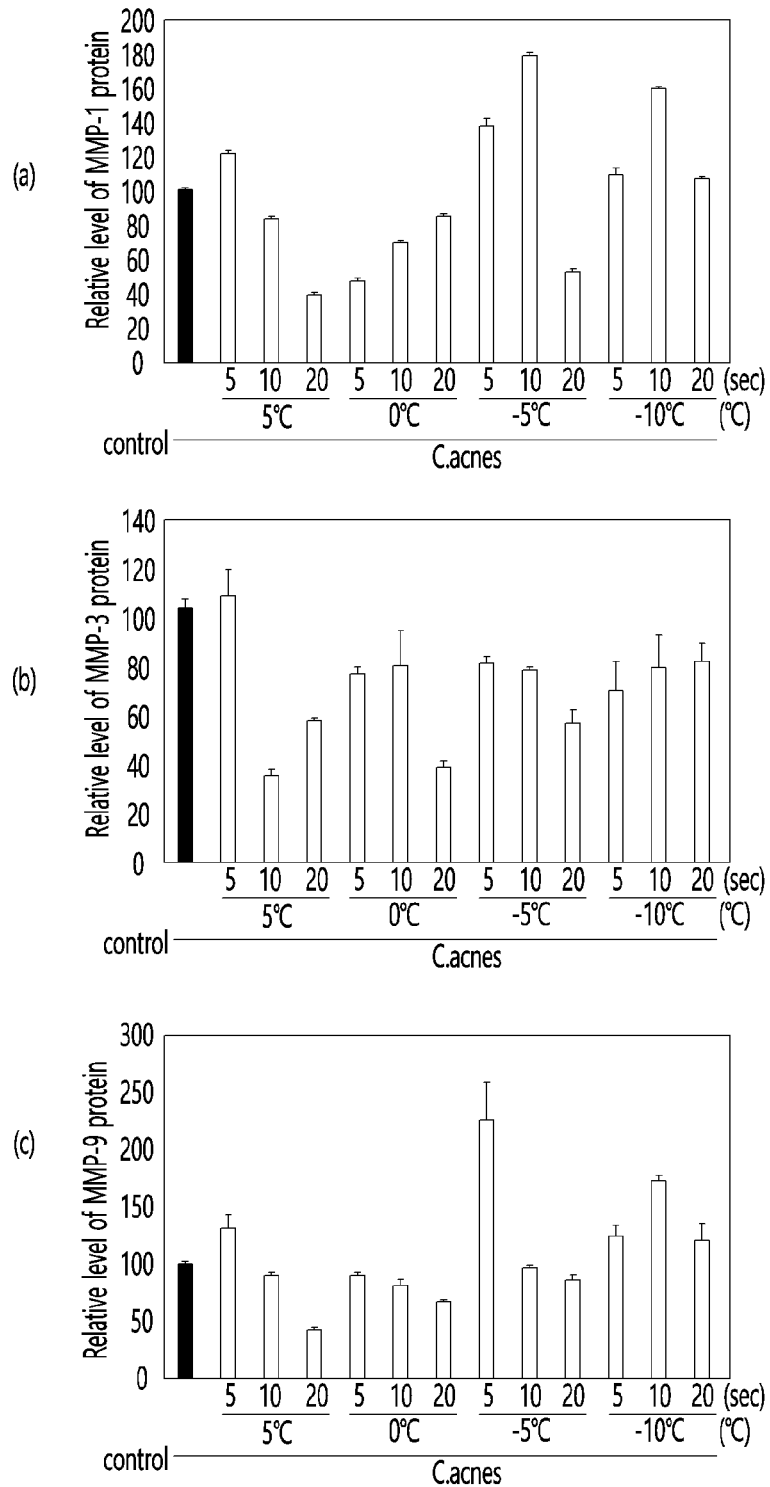

FIGS. 21 and 22 show graphs comparing and analyzing the expression level of protein biomarkers related to inflammatory acne, and the like; expression levels of protein biomarkers related to inflammatory acne in Group 1 to which the cooling treatment was performed and Group 2 to which the cooling treatment was not performed were compared and analyzed.

Referring to FIGS. 21 and 22, it was confirmed that in the case of Group 1 to which the cooling treatment was performed, the biomarkers related to inflammatory acne, etc. showed a tendency to be expressed relatively less than in the case of Group 2 which was not subjected to the cooling treatment, as shown below.

Referring to graph a of FIG. 21, in the case of IL1-β protein, it was confirmed in particular that the expression level was significantly lower when cooling treatment was performed as follows: ① at 5° C. for 5 and 10 seconds; ② at 0° C. for 5, 10 and 20 seconds; ③ at −5° C. for 5, 10 and 20 seconds; and ④ at −10° C. for 20 seconds.

Referring to graph b of FIG. 21, in the case of IL-6 protein, it was confirmed in particular that the expression level was significantly lower when cooling treatment was performed as follows: ① at 5° C. for 10 and 20 seconds; ② at 0° C. for 5, 10 and 20 seconds; ③ at −5° C. for 5 seconds; and ④ at −10° C. for 5 and 10 seconds.

Referring to graph c of FIG. 21, in the case of IL-8 protein, it was confirmed in particular that the expression level was significantly lower when cooling treatment was performed as follows: ① at 5° C. for 5, 10 and 20 seconds; ② at 0° C. for 5, 10 and 20 seconds; and ③ at −5° C. for 5 and 10 seconds.

Referring to graph d of FIG. 21, in the case of TNF-α protein, it was confirmed in particular that the expression level was significantly lower when cooling treatment was performed as follows: ① at 5° C. for 5, 10 and 20 seconds; and ② at 0° C. for 10 and 20 seconds.

Referring to graph a of FIG. 22, in the case of MMP-1 protein, it was confirmed in particular that the expression level was significantly lower when cooling treatment was performed as follows: ① at 5° C. for 10 and 20 seconds; ② at 0° C. for 5, 10 and 20 seconds; and ③ at −5° C. for 20 seconds.

Referring to graph b of FIG. 22, in the case of MMP-3 protein, it was confirmed in particular that the expression level was significantly lower when cooling treatment was performed as follows: ① at 5° C. for 10 and 20 seconds; ② at 0° C. for 5, 10 and 20 seconds; ③ at −5° C. for 5, 10 and 20 seconds; and ④ at −10° C. for 5, 10 and 20 seconds.

Referring to graph c of FIG. 22, in the case of MMP-9 protein, it was confirmed in particular that the expression level was significantly lower when cooling treatment was performed as follows: ① at 5° C. for 10 and 20 seconds; ② at 0° C. for 5, 10 and 20 seconds; and ③ at −5° C. for 10 and 20 seconds.

Through this analysis result, it was confirmed that protein biomarkers related to inflammatory acne were relatively less expressed when cooling treatment was performed at a specific temperature and for a specific time.

Therefore, it has been demonstrated that, if cooling treatment is performed to alleviate inflammatory acne, inflammatory acne can be alleviated by performing cooling treatment to control the affected area suspected of inflammatory acne to a specific temperature.

In addition, it has been demonstrated that, when cooling treatment is performed to alleviate inflammatory acne, inflammatory acne can be alleviated by performing cooling treatment for a specific time while controlling the affected area suspected of inflammatory acne to a specific temperature.

Figure 23:
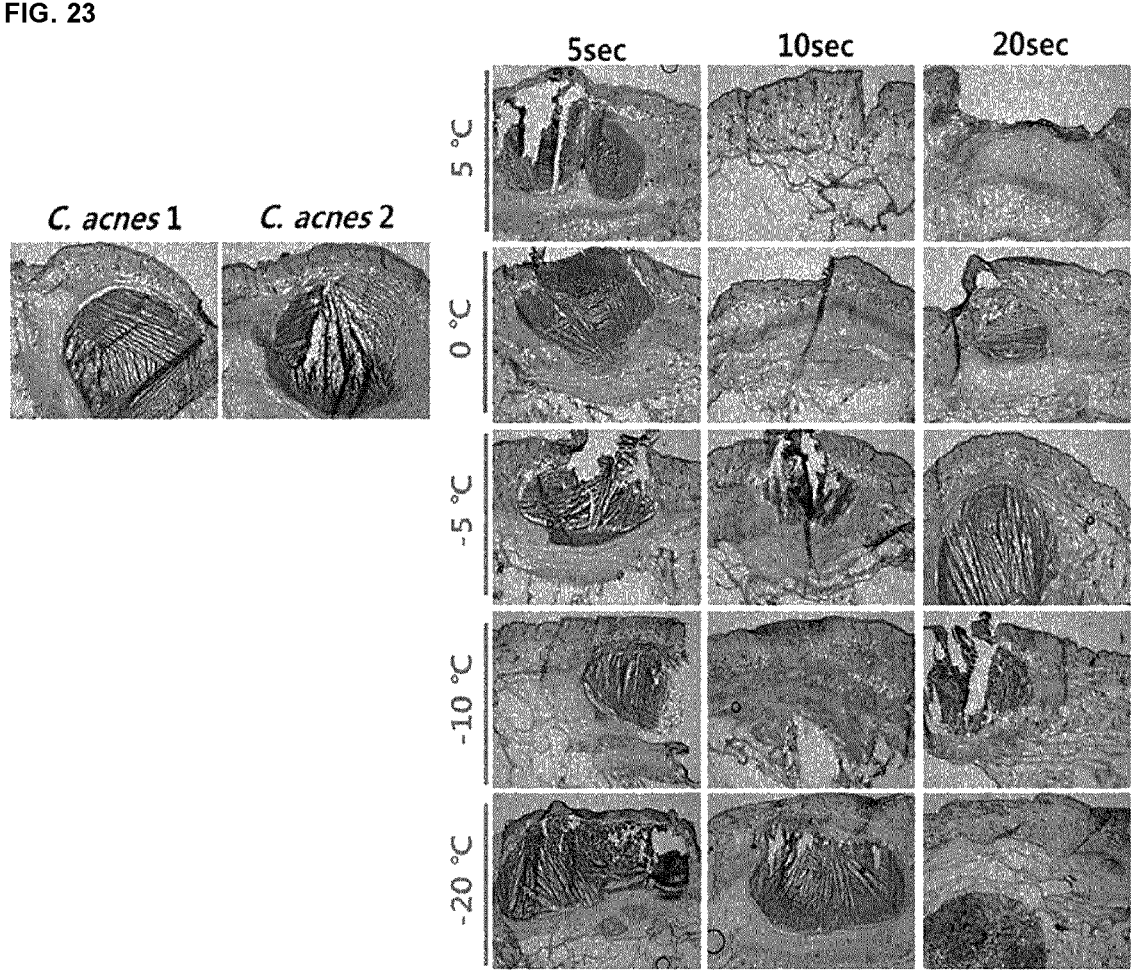

FIG. 23 is a diagram showing the results of staining a tissue sample through H&E staining after cooling treatment is performed on the inflammatory acne area.

As described above, after securing two acne lesion tissues from two mice per cooling condition, H&E staining was performed on acne lesions in order to observe histological changes in the cooling treatment site.

As a result, it was observed that the thickness of the lesion related to inflammatory acne was reduced in the group treated with C. acnes and subjected to the cooling treatment compared to the group treated with C. acnes and not subjected to the cooling treatment. In particular, it was observed that the thickness of the lesion related to inflammatory acne was significantly reduced when cooling treatment was performed ① at 5° C. for 10 seconds and 20 seconds, and ② at 0° C. for 10 seconds and 20 seconds.

Figure 24:
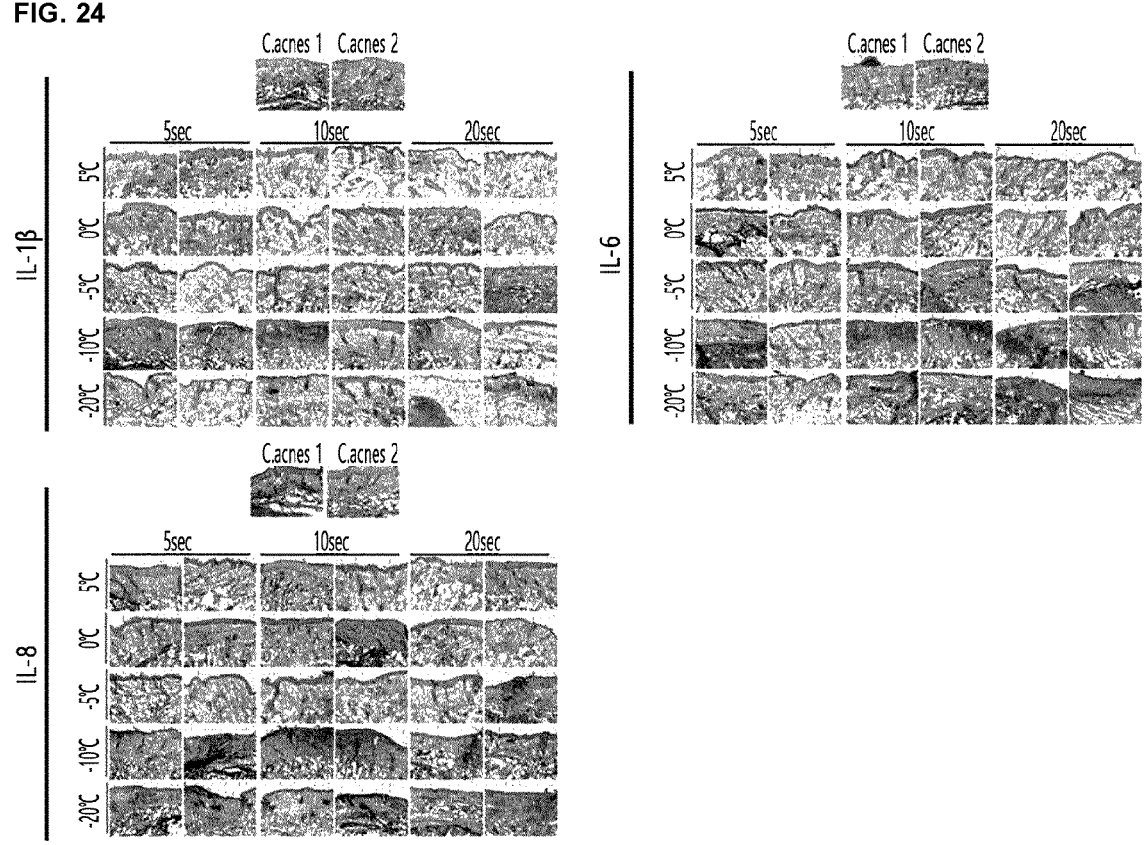
Figure 25:
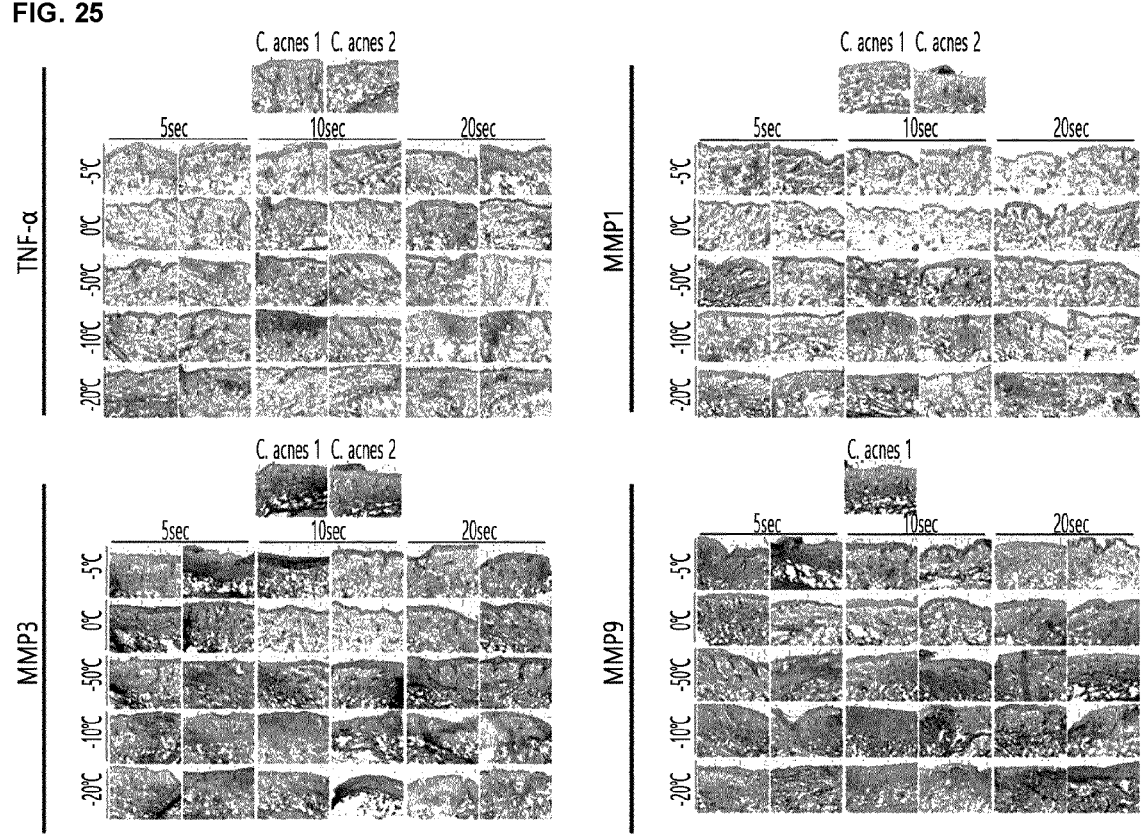

FIGS. 24 and 25 are diagrams showing the results of staining a tissue sample using an immunohistochemical method after performing a cooling treatment on an inflammatory acne site.

As described above, after securing two acne lesion tissues from two mice per cooling condition, immunostaining was performed for inflammatory antibodies and skin regeneration-related antibodies to observe histological changes in the area treated with cooling.

As a result, it can be confirmed that the expression of biomarkers related to inflammatory acne tends to be relatively decreased in the group treated with C. acnes and subjected to the cooling treatment than in the group treated with C. acnes and not subjected to cooling treatment.

In particular, for IL1-β, IL-6, IL-8, TNF-α, MMP-1, MMP-3 and MMP-9, it was observed that the degree of expression decreased under cooling conditions ① at 5° C. for 10 and 20 seconds, and ② at 0° C. for 10 and 20 seconds, as compared to the group treated with C. acnes and not subjected to cooling treatment.

On the other hand, part of the lesion tissue was observed to freeze under the cooling conditions of ① at −10° C., and ② at −20° C.; in particular, in the case of IL-6, IL-8, MMP-1, MMP-3 and MMP-9, it was visually confirmed that the level of expression was similar to that of the group treated with C. acnes and not subjected to cooling treatment.

Through this analysis result, it was visually confirmed that when the cooling treatment was performed at a specific temperature and for a specific time, the protein causing inflammatory acne was relatively less expressed. In particular, it was confirmed that the therapeutic effect of inflammatory acne is increased in the case of cooling and treating inflammatory acne at a specific temperature, such as −10° C. to 5° C.; through this, it can be inferred that treating inflammatory acne while controlling the cooling temperature can be advantageous in remarkably increasing the therapeutic effect.

4) Discussion

The cooling treatment method or the cooling treatment method performed in the above-described experiment may comprise a step of specifying the affected area as a target area; a step of setting the target temperature to −20° C., −10° C., −5° C., 0° C., or 5° C. and setting the cooling time to 5 seconds, 10 seconds, or 20 seconds; a step of disposing a cooling device relative to the target area; a step of operating a cooling device to spray a coolant on a target area, and applying thermal energy to the coolant using a temperature control means of the cooling device; a step of maintaining the temperature of the target area at the target temperature by measuring the temperature of the target area, so that if the measured temperature is lower than the set target temperature, the heat energy applied to the coolant per unit time is increased, and if the measured temperature is higher than the set target temperature, the thermal energy applied to the coolant per unit time is reduced; and a step of terminating the cooling treatment for the target area when the time during which the temperature of the target area is maintained at the target temperature is at least the set cooling time. In this case, this means that, in the step of maintaining the target region at the target temperature, the temperature of the target region is maintained within an error range (for example, the error range is selected from 0.00° C. to 2.00° C.) at the target temperature.

Considering the experimental results, cooling treatment that maintains the affected area at −20° C., −10° C., −5° C., 0° C., or 5° C. for at least 5 seconds, 10 seconds, or 20 seconds enables effective alleviation of the symptoms of inflammatory acne in the affected area by reducing the expression of biomarkers related to inflammatory acne.

The biomarker related to inflammatory acne may refer to at least one biomarker of IL1-α, IL-1β, IL-6, IL-8, TNF-α, MMP-1, MMP-3, and MMP-9.

Referring to the analysis result shown in FIG. 18, it was confirmed that, when cooling treatment is performed on the inflammatory acne lesion under the cooling conditions described above, the sizes of the inflammatory acne lesions tended to be relatively smaller under all cooling conditions than in the case where cooling treatment was not performed. In particular, it was confirmed that the sizes of the inflammatory acne lesions were significantly reduced when the cooling treatment was performed at a temperature of −5° C., 0° C., or 5° C. for 5 seconds, 10 seconds, or 20 seconds.

When considering the analysis results related to FIGS. 19 and 20, it was quantitatively confirmed that the expression level of most of the gene biomarkers related to inflammatory acne was relatively low in the treatment group to which the cooling treatment was performed compared to the control group to which the cooling treatment was not performed.

In addition, when considering the analysis results related to FIGS. 21 and 22, it was quantitatively confirmed that the expression levels of most of the gene biomarkers as well as the protein biomarkers related to inflammatory acne were relatively low in the treatment group to which the cooling treatment was performed compared to the control group to which the cooling treatment was not performed.

Especially at the genetic level, for the IL1-α gene and IL1-β gene, known as representative biomarkers of inflammatory acne, it was confirmed that the expression level was significantly lower when cooling treatment was performed at all cooling conditions of ① at 5° C. for 5, 10 and 20 seconds; ② at 0° C. for 5, 10 and 20 seconds; ③ at −5° C. for 5, 10 and 20 seconds; and ④ at −10° C. for 5, 10 and 20 seconds; than in the case where cooling treatment was not performed.

At the protein level, for the IL1-α protein and IL1-β protein, known as representative biomarkers of inflammatory acne, it was confirmed that the expression level was significantly lower when cooling treatment was performed ① at 5° C. for 5 and 10 seconds; ② at 0° C. for 5, 10 and 20 seconds; ③ at −5° C. for 5, 10 and 20 seconds; and ④ at −10° C. for 20 seconds.

Through this analysis result, it was confirmed that, for lesions associated with inflammatory acne, when the cooling treatment is performed for a specific time (for example, 5 seconds to 20 seconds) while maintaining the temperature of the affected area at a specific temperature (for example, a temperature range of −20° C. to 5° C.), the sizes of inflammatory acne lesions tend to decrease significantly, and the expression of biomarkers related to inflammatory acne showed a tendency to significantly decrease.

Referring to the analysis results related to FIGS. 24 and 25, when cooling treatment was performed on inflammatory acne lesions under the above-described cooling conditions, it was visually confirmed that antibodies bound to biomarkers related to inflammatory acne, etc. were detected to be relatively low. The finding that the antibody binding to the biomarker was detected to be relatively low means that there are fewer biomarkers in the form of expressed proteins; therefore, this analysis result lends further support to the supposition that the therapeutic effect of inflammatory acne lesions is increased, in consideration of the result that the expression of protein biomarkers related to inflammatory acne is significantly reduced when the temperature of the affected area associated with the inflammatory acne lesion is maintained at a specific temperature (for example, a temperature range of −20° C. to 5° C.), and cooling treatment is performed for a specific time (for example, 5 seconds to 20 seconds).

However, a part of the lesion tissue was frozen under the cooling conditions of ① at −10° C. ② at −20° C. Further, under the cooling conditions of ① at −10° C., ② at −20° C., it was confirmed that the expression level of some biomarkers such as IL-6, IL-8, MMP-1, MMP-3 and MMP-9 was similar to or higher than the expression level of the group treated with C. acnes and not subjected to cooling treatment.

In addition, referring back to the analysis results related to FIG. 18, it can be confirmed that the size of inflammatory acne was not significantly improved when the cooling treatment was performed at a temperature of −20° C. In particular, it can be confirmed that, when cooling treatment was performed for 10 seconds or 20 seconds at a temperature of −20° C., the size of inflammatory acne was significantly larger than that of the control group where cooling treatment was not performed.

Through this analysis result, as with itching, in performing cooling treatment to treat inflammatory acne, it has been confirmed once again that cooling conditions comprising cooling temperature and/or cooling time are very important factors. Therefore, in performing cooling treatment to treat inflammatory acne, cooling conditions comprising cooling temperature and/or cooling time must be selected and controlled very precisely.

Combining the above analysis results, according to a preferred embodiment, the target temperature for alleviating the symptoms of inflammatory acne may be selected as a temperature of 0° C. or higher and 5° C. or lower. The cooling time of the target area may be selected within at least 5 seconds to 20 seconds.

By combining the above-described target temperature and cooling time, the target temperature is selected from a temperature of 0° C. or higher and 5° C. or lower, and the cooling time may be selected within at least 5 seconds to 20 seconds.

More preferably, the target temperature may be selected from 0° C. or higher and 5° C. or lower, and the cooling time may be selected to be about 20 seconds.

(2) Clinical Study

Hereinafter, experiments performed on patients suffering from inflammatory acne disease will be described in order to prove the effect of alleviating the symptoms of inflammatory acne through the cooling treatment method using the above-described precision cooling technology.

1) Experimental Method

Patients with symptoms of inflammatory acne were selected as study subjects.

Some of the experimental subjects were treated with a cooling device (Recensmedical, Cryo-VIVE, Korea) as a treatment group, and cooling treatment was performed.

Among the experimental subjects, patients aside from the treatment group were observed as a control group without cooling treatment.

For the experimental subjects in the treatment group, the treatment was carried out by spraying a coolant on the affected area for about 5 seconds using a cooling device so that the affected area showing symptoms of inflammatory acne was maintained at −5° C.

The cooling treatment method performed in the experiment comprises a step of specifying the area suspected of itching as the target area, setting the target temperature to −5° C. and setting the cooling time to 5 seconds; a step of disposing a cooling device relative to the target area; a step of operating the cooling device to spray a coolant on a target area, and applying thermal energy to the coolant using a temperature control means of the cooling device; a step of maintaining the temperature of the target area at −5° C. by measuring the temperature of the target area, so that if the measured temperature is lower than −5° C., the heat energy applied to the coolant per unit time is increased, and if the measured temperature is higher than −5° C., the thermal energy applied to the coolant per unit time is reduced; and a step of terminating the cooling treatment for the target area when the time the temperature of the target area is maintained at −5° C. is at least 5 seconds. At this time, in the step of maintaining the target area at the target temperature of −5° C., the temperature of the target area is maintained within the error range (for example, the error range is selected from 0.00° C. to 2.00° C.) at −5° C. Also, the diameter of the affected area specific to the target area is about 15 mm.

2) Experiment Result

Figure 26:
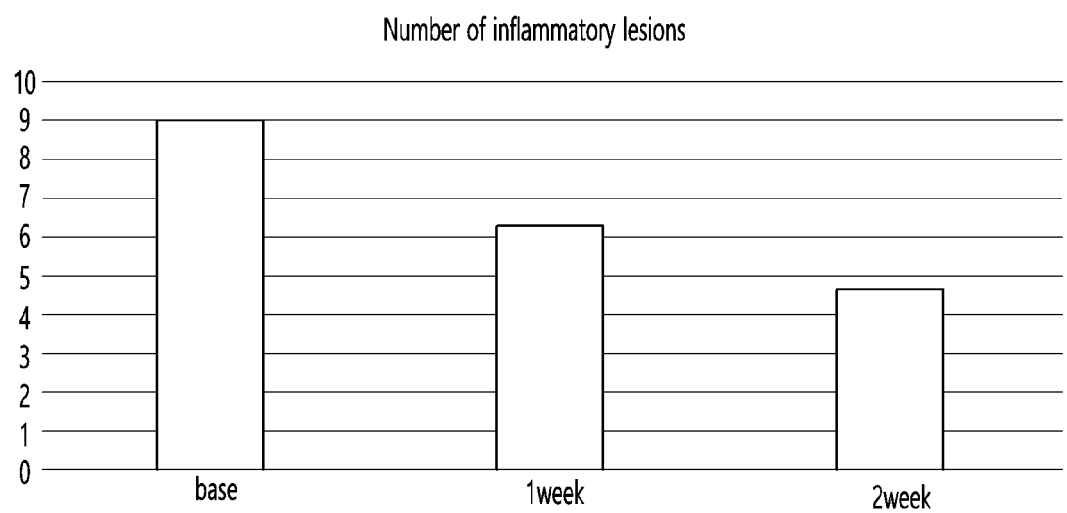

FIG. 26 is a graph showing the number of inflammatory acne lesions in patients in a treatment group.

Referring to FIG. 26, it can be seen that the number of inflammatory acne lesions in the patients in the treatment group that received the cooling treatment gradually decreased after the cooling treatment was performed.

Specifically, while the average number of inflammatory acne lesions in the patients in the treatment group before cooling treatment was 9, it was confirmed that the number of inflammatory acne lesions gradually decreased, as follows: ① at one week after cooling treatment, the average number of inflammatory acne lesions in the treatment group was about 6.2; ② at 2 weeks after cooling treatment, the average number of inflammatory acne lesions in the treatment group was about 4.7.

3) Analysis of Experimental Results

Through the results of this experiment, it was confirmed that the number of lesions, which is the most important index related to inflammatory acne, gradually decreased from the time of cooling treatment and improved.

By this means, it can be verified that when performing cooling treatment to alleviate inflammatory acne, if cooling treatment is performed while controlling the affected area suspected of inflammatory acne to a specific temperature, the symptoms of inflammatory acne can be improved.

Features, structures, effects, etc. described in the above embodiments are included in at least one embodiment of the present invention, and are not necessarily limited to only one embodiment. Furthermore, the features, structures, effects, etc. illustrated in each embodiment can be combined or modified for other embodiments by those of ordinary skill in the art to which the embodiments belong. Accordingly, the contents related to such combinations and modifications should be interpreted as being included in the scope of the present invention.

In addition, although the embodiments have been mainly described above, they are only examples and do not limit the present invention; those of ordinary skill in the art pertaining to the present invention will appreciate that various modifications and applications not exemplified above are possible without departing from the essential characteristics of the present embodiment. That is, each component specifically shown in the embodiment can be implemented by modification, and differences related to such modifications and applications should be construed as being included in the scope of the present invention defined in the appended claims.

The invention claimed is:

1. A method of treating a skin rash or relieving a symptom associated with a skin rash using a cooling device in a subject, comprising:
cooling a target skin area affected by the skin rash using the cooling device at a target temperature selected from about −5° C. to about 5° C. for a target cooling time, wherein a temperature of the target skin area is maintained at a temperature with a standard deviation no larger than 3° C. from the target temperature during the target cooling time, and
wherein the target temperature and the target cooling time are selected to be sufficient to reduce an expression of biomarker molecules comprising at least one of IL-4, IL-10, IL-13, or IL-31, which are associated with the skin rash or the symptom.

2. The method of claim 1, wherein the skin rash or the symptom associated with the skin rash comprises atopic dermatitis, itchiness, or acne.

3. The method of claim 1, wherein the target temperature and the target cooling time are selected to be sufficient to reduce mRNA or protein expression level of the biomarker molecules by at least 20%, at least 30%, at least 40%, or at least 50%.

4. The method of claim 1, wherein the target skin area is cooled to the target temperature in less than 20 seconds.

5. The method of claim 1, wherein the target cooling time is between about 1 second to about 30 seconds.

6. The method of claim 1, wherein the target cooling time is less than about 5 seconds, less than about 10 seconds, less than about 20 seconds, less than about 30 seconds, or less than about 60 seconds.

7. The method of claim 1, wherein the biomarker molecules further comprise TRPV1, TRPA1, IFN-γ, and PAR2.

8. The method of claim 1, wherein the biomarker molecules further comprise IL-1β, IL-6, IL-7, TNFα, MMP1, MMP3, and MMP9.

9. The method of claim 1, wherein the biomarker molecules include IL-31, and the target temperature and the target cooling time are selected to be sufficient to reduce mRNA or protein expression level of IL-31 by at least 30%.

10. The method of claim 1, wherein the skin target area has a diameter less than about 2 cm, or has a size of less than about 7 cm$^2$.

11. The method of claim 1, wherein the symptom associated with the skin rash is relieved for at least a day after the treatment to the subject, determined by a visual analogue scale (VAS) score of the subject.

12. The method of claim 1, wherein the cooling device comprises a temperature sensor, a cryogen, and a control module, the method further comprising:
detecting the temperature of the target skin area by the temperature sensor; and
maintaining the temperature of the target skin area by a control module configured to control a temperature of the cryogen based on the temperature of the target skin area during the operation of the cooling device.

13. The method of claim 12, wherein the cooling device further comprises a guide unit and a nozzle, wherein the method further comprises detecting a distance from the target skin area to the nozzle using the guide unit.

14. The method of claim 13, wherein the cryogen comprises $CO_2$, liquid nitrogen, $NO_2$, NO, $N_2O$, HFC, methane, PFC, or SF6.

15. The method of claim 12, wherein the cooling the target skin area comprises spraying the cryogen directly to the target skin area through a nozzle of the cooling device.

16. A method of reducing an expression of biomarker molecule related to itching using a cooling device configured to cool a skin target area with a target temperature for a preset time duration, the method comprising:
preparing the cooling device including a housing, a temperature sensor, a control module, and a nozzle, wherein the control module is configured to control a temperature of a cryogen which is transferred from a container to the nozzle according to a detected temperature by the temperature sensor;
positioning the cooling device on a patient's skin such that the skin target area is defined;
cooling the skin target area such that a temperature of the skin target area reaches the target temperature, which comprises spraying the cryogen to the skin target area directly; and
maintaining the temperature of the skin target area at the target temperature for the preset time duration, which comprises detecting the temperature of the skin target area, and increasing or decreasing the temperature of the cryogen when the temperature of the skin target area is lower or higher than the target temperature while the cryogen is consistently sprayed;
wherein the target temperature is selected from −5° C. to 5° C. such that the expression of the biomarker molecule selected from a group consisting of interleukin-4, interleukin-10, interleukin-13, or interleukin-31 at the skin target area is reduced.

17. The method of claim 16, wherein during the preset time duration, the temperature of the skin target area is maintained at a temperature with a standard deviation no larger than 3° C. from the target temperature.

18. The method of claim 16, wherein the cooling time is selected below 20 seconds.

19. The method of claim 16, further comprising:
setting the target temperature and the preset time duration by using an input module of the cooling device.

20. The method of claim 19, wherein the target temperature is set as 0° C. and the preset time duration is set as 5 seconds when the skin target area is a part of the patient's face.

21. The method of claim 19, wherein the target temperature is set as −5° C. and the preset time duration is set as 5 seconds when the skin target area is a part of the patient's body.

22. The method of claim 16, further comprising:
removing the cooling device from the skin target area or moving to another skin target area when a notification is provided such that the skin target area is cooled for the preset time duration only, wherein the notification is provided when the preset time duration is past after the temperature of the skin target area reaches the target temperature.

23. The method of claim 16, further comprising:
reducing the expression of the biomarker molecule selected from a group consisting of interleukin-4 mRNA, interleukin-10 mRNA, interleukin-13 mRNA, and interleukin-31 mRNA.

24. The method of claim 16, further comprising:
reducing the expression of the biomarker molecule selected from a group consisting of TRPV1, TRPA1, IFN-γ, and PAR2.

25. The method of claim 1, wherein the target temperature is selected from 0° C. to about 5° C. to reduce expression of the biomarker molecules comprising at least one of IL-4, IL-10, IL-13, or IL-31.

26. The method of claim 1, wherein the target temperature is selected from 0° C. to about 5° C. and the target cooling time is selected from 5 seconds to 20 seconds to reduce expression of the biomarker molecules comprising at least one of IL-4, IL-10, IL-13, or IL-31.

\* \* \* \* \*

UNITED STATES PATENT AND TRADEMARK OFFICE
CERTIFICATE OF CORRECTION

PATENT NO. : 12,364,531 B2  
APPLICATION NO. : 17/590694  
DATED : July 22, 2025  
INVENTOR(S) : Gun-Ho Kim Page 1 of 2

It is certified that error appears in the above-identified patent and that said Letters Patent is hereby corrected as shown below:

In the Drawings

Sheet 4 of 26, FIG. 4, Line 12 (approx.), delete "10min later" and insert --10 min later--.

Sheet 5 of 26, FIG. 5, Line 13 (approx.), delete "10min later" and insert --10 min later--.

Sheet 18 of 26, FIG. 18, Line 1 (Y-Axis), delete "Leslon dlameter(mm)" and insert --Lesion diameter (mm)--.

Sheet 18 of 26, FIG. 18, Line 1 (Y-Axis), delete "Leslon dlameter(mm)" and insert --Lesion diameter (mm)--.

Sheet 18 of 26, FIG. 18, Line 1 (Y-Axis), delete "Leslon dlameter(mm)" and insert --Lesion diameter (mm)--.

Sheet 26 of 26, FIG. 26, Line 1 (X-Axis), delete "1week" and insert --1 week--.

Sheet 26 of 26, FIG. 26, Line 1 (X-Axis), delete "2week" and insert --2 week--.

In the Specification

Column 20, Line 38, delete "7 μm and" and insert --7 μm, and--.

Column 20, Line 52, delete "time, 3-amino9-ethylcarbazole" and insert --time, 3-amino-9-ethylcarbazole--.

Column 25, Line 39, delete "IFN-γ protein" and insert --IFN-γ protein.--.

Column 27, Line 3, delete "Il-6 (1:200" and insert --Il-6 (1:200--.

Signed and Sealed this  
Twenty-eighth Day of October, 2025

John A. Squires  
*Director of the United States Patent and Trademark Office*

CERTIFICATE OF CORRECTION (continued)
U.S. Pat. No. 12,364,531 B2

Column 27, Line 4, delete "Il-8 (1:200" and insert --Il-8 (1:200--.

Column 27, Line 9, delete "dilution; Abcam,)," and insert --dilution; Abcam).--.

Column 27, Line 38, delete "at 5000λ for" and insert --at 5000X for--.

Column 28, Line 45, delete "Il-6 (1:200" and insert --Il-6 (1:200--.

Column 28, Line 45, delete "Il-8 (1:200" and insert --Il-8 (1:200--.

Column 28, Line 54, delete "time, 3-amino9-ethylcarbazole" and insert --time, 3-amino-9-ethylcarbazole--.

Column 31, Line 16, delete "of MMP 1, it" and insert --of MMP1, it--.

Column 31, Line 42, delete "IL-1β, Il-6, TNF-α," and insert --IL-1β, Il-6, TNF-α,--.

In the Claims

Column 38, Claim 16, Line 18, delete "expression of biomarker" and insert --expression of at least one biomarker--.

Column 38, Claim 16, Line 42, delete "of the biomarker" and insert --of the at least one biomarker--.

Column 39, Claim 23, Line 5, delete "of the biomarker" and insert --of the at least one biomarker--.

Column 39, Claim 24, Line 10, delete "of the biomarker" and insert --of the at least one biomarker--.